(12) United States Patent
Sze

(10) Patent No.: US 9,349,175 B2
(45) Date of Patent: *May 24, 2016

(54) APPARATUS, SYSTEM, AND PROCESS FOR DETERMINING CHARACTERISTICS OF A SURFACE OF A PAPERMAKING FABRIC

(71) Applicant: Georgia-Pacific Consumer Products LP, Atlanta, GA (US)

(72) Inventor: Daniel H. Sze, Appleton, WI (US)

(73) Assignee: Georgia-Pacific Consumer Products LP, Atlanta, GA (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/077,808

(22) Filed: Nov. 12, 2013

(65) Prior Publication Data
US 2014/0133734 A1 May 15, 2014

Related U.S. Application Data

(60) Provisional application No. 61/725,749, filed on Nov. 13, 2012.

(51) Int. Cl.
*D21F 1/10* (2006.01)
*D21F 7/08* (2006.01)
(Continued)

(52) U.S. Cl.
CPC . *G06T 7/001* (2013.01); *D21F 7/06* (2013.01); *D21F 7/08* (2013.01); *D21F 11/006* (2013.01);
(Continued)

(58) Field of Classification Search
CPC ... D21F 1/0027; D21F 1/0036; D21F 1/0045; D21F 1/10; D21F 1/105; D21F 1/30; D21F 5/18; D21F 7/08; D21F 7/053; D21F 7/12; D21F 11/006; D21F 11/008; D21F 11/14; D21F 11/145; D21G 9/0036; G06T 2200/04; G06T 2207/30124; G06T 7/40; G06T 7/0059; G06T 7/0063; G06T 15/04
USPC ............. 162/198, 199, 263, 272, 348, 900, 162/902–904; 139/383 A, 1 B; 382/111, 382/141; 73/159, 7; 26/70; 356/238.1, 356/237.5, 429–431, 921
See application file for complete search history.

(56) References Cited

U.S. PATENT DOCUMENTS 3,905,863 A * 9/1975 Ayers ........................... 162/113
4,142,557 A   3/1979 Kositzke
(Continued)

FOREIGN PATENT DOCUMENTS

DE   19917832 A1   11/2000
EP    1413674 A1    4/2004
(Continued)

OTHER PUBLICATIONS

Notification of International Search Report and Written Opinion mailed Aug. 1, 2014, in counterpart PCT Publication No. PCT/US2014/038999.
(Continued)

*Primary Examiner* — Eric Hug
(74) *Attorney, Agent, or Firm* — Laura L. Bozek

(57) ABSTRACT

Apparatuses, processes, and systems for implementing techniques for determining characteristics of a papermaking fabric. The techniques include forming a representation of a portion of the surface of the fabric, with the representation showing the knuckles and pockets in the surface. The representation can be formed, for example, in pressure measurement film, in wax paper, or as a photograph. An image is generated from the representation, and the image is analyzed to determine characteristics of the surface of the fabric, such as knuckle sizes and pocket sizes. The depth of pockets in the fabric can also be determined. The techniques can be used in processes for analyzing wear of a fabric, and for obtaining a fabric for making a paper product with a particular three-dimensional structure.

23 Claims, 12 Drawing Sheets

(51) Int. Cl.
*D21F 7/12* (2006.01)
*G06T 7/40* (2006.01)
*G06T 7/00* (2006.01)
*D21F 11/00* (2006.01)
*G01L 1/00* (2006.01)
*D21G 9/00* (2006.01)
*D21F 7/06* (2006.01)
*G01N 3/56* (2006.01)

(52) U.S. Cl.
CPC ............ *D21G 9/0036* (2013.01); *G01L 1/00* (2013.01); *G06T 7/0006* (2013.01); *G01N 3/56* (2013.01); *G06T 2200/04* (2013.01); *G06T 2207/10028* (2013.01); *G06T 2207/30124* (2013.01)

(56) References Cited

U.S. PATENT DOCUMENTS

| | | | |
|---|---|---|---|
| 4,191,609 A * | 3/1980 | Trokhan | 162/113 |
| 5,542,455 A | 8/1996 | Ostermayer et al. | |
| 5,832,962 A * | 11/1998 | Kaufman et al. | 139/383 A |
| 6,039,838 A * | 3/2000 | Kaufman et al. | 162/109 |
| 6,350,336 B1 | 2/2002 | Paquin | |
| 6,592,714 B2 * | 7/2003 | Lamb | 162/116 |
| 6,649,026 B2 | 11/2003 | Lamb | |
| 6,787,000 B2 | 9/2004 | Burazin et al. | |
| 7,207,356 B2 | 4/2007 | Patel et al. | |
| 7,294,234 B2 | 11/2007 | Münch et al. | |
| 7,493,923 B2 * | 2/2009 | Barrett et al. | 139/383 A |
| 7,494,563 B2 | 2/2009 | Edwards et al. | |
| 7,611,607 B2 | 11/2009 | Mullally et al. | |
| 7,644,738 B2 | 1/2010 | Kroll et al. | |
| 7,662,462 B2 | 2/2010 | Noda et al. | |
| 7,873,433 B2 | 1/2011 | Böck et al. | |
| 7,955,549 B2 | 6/2011 | Noda et al. | |
| 7,993,493 B2 | 8/2011 | Quigley | |
| 8,328,990 B2 | 12/2012 | Quigley | |
| 8,722,173 B2 | 5/2014 | Oba et al. | |
| 8,857,370 B2 | 10/2014 | Kida et al. | |
| 2003/0085013 A1 | 5/2003 | Burazin et al. | |
| 2004/0266296 A1 | 12/2004 | Martinsson et al. | |
| 2006/0003655 A1 | 1/2006 | Patel et al. | |
| 2007/0298667 A1 | 12/2007 | Noda et al. | |
| 2008/0029235 A1 * | 2/2008 | Edwards et al. | 162/111 |
| 2008/0044628 A1 | 2/2008 | Noda et al. | |
| 2008/0085399 A1 | 4/2008 | Noda et al. | |
| 2008/0110591 A1 * | 5/2008 | Mullally et al. | 162/358.2 |
| 2009/0282660 A1 | 11/2009 | Noda et al. | |
| 2010/0186922 A1 * | 7/2010 | Quigley | 162/358.1 |
| 2012/0045620 A1 | 2/2012 | Oba et al. | |
| 2012/0141742 A1 | 6/2012 | Yamaguchi et al. | |
| 2012/0177889 A1 | 7/2012 | Uematsu et al. | |
| 2012/0328772 A1 | 12/2012 | Kida et al. | |
| 2014/0130996 A1 | 5/2014 | Sze | |

FOREIGN PATENT DOCUMENTS

| | | |
|---|---|---|
| EP | 2204492 A1 | 7/2010 |
| WO | 97/24488 A1 | 7/1997 |
| WO | 2005/113893 A1 | 12/2005 |
| WO | 2008/114221 A1 | 9/2008 |

OTHER PUBLICATIONS

International Search Report completed Jun. 10, 2014, and mailed Jul. 2, 2014, in counterpart International Patent Application No. PCT/US2013/069899.

Written Opinion mailed Jul. 2, 2014, in counterpart International Patent Application No. PCT/US2013/069899.

Simmonds, Glen E., et al. "Designing Nonwovens to Meet Pore Size Specifications," Journal of Engineered Fibers and Fabrics, vol. 2, No. 1, Dec. 31, 2007, pp. 1-15.

* cited by examiner

APPARATUS, SYSTEM, AND PROCESS FOR DETERMINING CHARACTERISTICS OF A SURFACE OF A PAPERMAKING FABRIC

This application claims the benefit of priority of U.S. Provisional Patent Application No. 61/725,749, filed Nov. 13, 2012.

BACKGROUND

1. Field of the Invention

My invention relates to characterizing the surface of a papermaking fabric. In specific examples, my invention relates to apparatuses, processes, and systems for determining the characteristics of the contact surface of a fabric that is used for three-dimensional structuring of a web in a papermaking process.

2. Related Art

In processes of forming paper products, such as tissue paper and paper towels, three-dimensional shaping is conducted while the papermaking web is still highly deformable, i.e., when the papermaking web has a high water content. Often, this three-dimensional shaping of the web is conducted on a woven structuring fabric. The fabric provides a contact surface made up of knuckles in the yarns of the fabric, with pockets being formed in the fabric between the knuckles. When the papermaking web is applied to the fabric, portions of the web contact the knuckles, and other portions of the web are drawn into the pockets. Before being removed from the fabric, the web is dried to a point such that its shape is fixed or locked. Domes are thereby formed in the dried web where the web was drawn into the pockets in the fabric, and the domes are present in the finished paper product. Hence, the paper product has a distinct three-dimensional structure formed, in part, by the knuckle and pocket characteristics of the structuring fabric.

Because the contact surface of a structuring fabric directly relates to the shape of the finished product, the choice of a structuring fabric is often based on the shape of the product that is desired. It is difficult, however, to characterize the contact surface of a structuring fabric based on a simple visual inspection of the fabric. While the knuckles of the fabric can easily be seen, it is often difficult to accurately determine the sizes of the knuckles, difficult to determine the areas of the pockets between the knuckles, and difficult to determine the depth of the pockets into which the papermaking web is drawn during the papermaking process. As such, there have been previous techniques that attempt to quantify the characteristics of the contact surface of the fabric, for example, using formulas based on the yarn parameters of the fabric. It has been found, however, that such formulas are often not accurate enough to characterize the contact surface of the fabric in a manner that allows for an accurate prediction of the paper product structure that will be formed with the fabric. Additionally, the contact area characteristics will often change as the fabric is run on a papermaking machine. For example, wear on the surface of the fabric will generally increase the lengths of the knuckles, thereby changing the structuring that will be imparted on the web by the fabric. Thus, formulas for determining the contact surface characteristics that are applicable to initial fabric configurations will not necessarily apply to fabrics that have become worn over time.

It would be beneficial, therefore, to provide a technique for accurately characterizing the contact area characteristics of a structuring fabric that is used in a papermaking process. Moreover, it would be beneficial to provide a technique that can easily determine the contact area characteristics as the fabric becomes worn, over time, while the fabric is mounted on a papermaking machine.

SUMMARY OF THE INVENTION

According to a first aspect, my invention provides a system for forming a print of the surface of a fabric. The system includes a first plate and a second plate. The system also includes a pressure measurement film, and a fabric that can be used in a papermaking process, with the fabric including a plurality of knuckles on at least one of its surfaces. A print of the knuckles of the fabric is formed on the pressure measurement film by pressing the fabric against the pressure measurement film between the first plate and the second plate.

According to another aspect, my invention provides a process of determining the features of a fabric. The process includes forming a representation of a portion of a surface of the fabric, with the representation showing the knuckles and pockets in the surface of the fabric. An image is generated of the portion of the fabric based on the representation, with the image showing the knuckles and the pockets, and at least a portion of the image is displayed on a screen associated with a computer having a processor. An outline is drawn around at least one of the knuckles in the displayed image. Guidelines are drawn in the displayed image such that the guidelines (i) pass through the center of the outlined knuckle, (ii) pass through the other knuckles, and (iii) do not pass through areas of the image that correspond to where the pockets are formed between the knuckles. The outline and the guidelines axe drawn using an image analysis program that is stored on a non-transitory computer-readable medium.

According to yet another aspect, my invention provides a process of analyzing wear on a papermaking fabric. The process includes forming a first representation of a portion of a surface of the fabric, the first representation showing knuckles and pockets in the surface of the fabric. A first image is generated based on the first representation. At least one characteristic related to the surface of the fabric using the first image is determined. The fabric is subjected to wearing. A second representation of a portion of the surface of the fabric is thereafter formed, with the second representation showing knuckles and pockets in the surface of the fabric. A second image of the fabric is generated based on the second representation, and at least one characteristic related to the surface of the fabric using the second image is determined. The determining steps are performed using an image analysis program that is stored in a non-transitory computer readable medium.

According to still another aspect, my invention provides a process of obtaining a fabric. An image of a paper product having a three-dimensional structure is obtained, and a pattern is determined that corresponds to the three-dimensional structure of the paper product, the pattern being determined by using an image analysis program that is stored in a non-transitory computer-readable storage medium to analyze the image of the paper product. A fabric is obtained with a surface that approximates the pattern.

According to a further aspect, my invention provides a process of determining the depth of pockets in a fabric. The process includes forming a representation of a portion of a surface of the fabric, with the representation showing locations and sizes of knuckles and pockets in the surface of the fabric. The process also includes identifying the knuckles surrounding a pocket in the fabric, and determining a path that passes from a first of the knuckles across the pocket to a second of the knuckles. The process further includes scanning the fabric using a measurement device along a line that corresponds to the determined path, and determining a depth profile of a pocket based on the scan of the fabric.

According to a yet further aspect, my invention provides a process of forming a papermaking fabric. The process includes determining the value of at least one characteristic of a first papermaking fabric, the at least one characteristic being related to at least one of knuckles and pockets formed in the first papermaking fabric, and forming a second papermaking fabric such that a value of the at least one characteristic in the second papermaking fabric is different from the value of the at least one characteristic in the first papermaking fabric.

DETAILED DESCRIPTION OF THE INVENTION

My invention relates to apparatuses, processes, and systems for determining the characteristics of the contact surface of a fabric that is used in a papermaking process. As will, be apparent from the discussion below, "characteristics of the contact surface of fabric" refers to the characteristics of the contact surface that result from the knuckle and pocket configuration that makes up the contact surface of the fabric. In specific embodiments, my invention is adapted for use with structuring fabrics that are used for three-dimensional structuring of a web in a papermaking process. Such structuring fabrics are often constructed with yarns made from, for example, polyethylene terephthalate (PET), polyester, polyamide, polypropylene, and the like. As will be further explained below, the particular contact surface of a structuring fabric will have a significant effect on the structure of the paper product, and my invention utilizes techniques for characterizing aspects of the contact surface. It should be noted, however, that my invention is applicable with any type of fabric that is used in a papermaking process, including fabrics that are used for purposes other than structuring the web.

Figure 1:
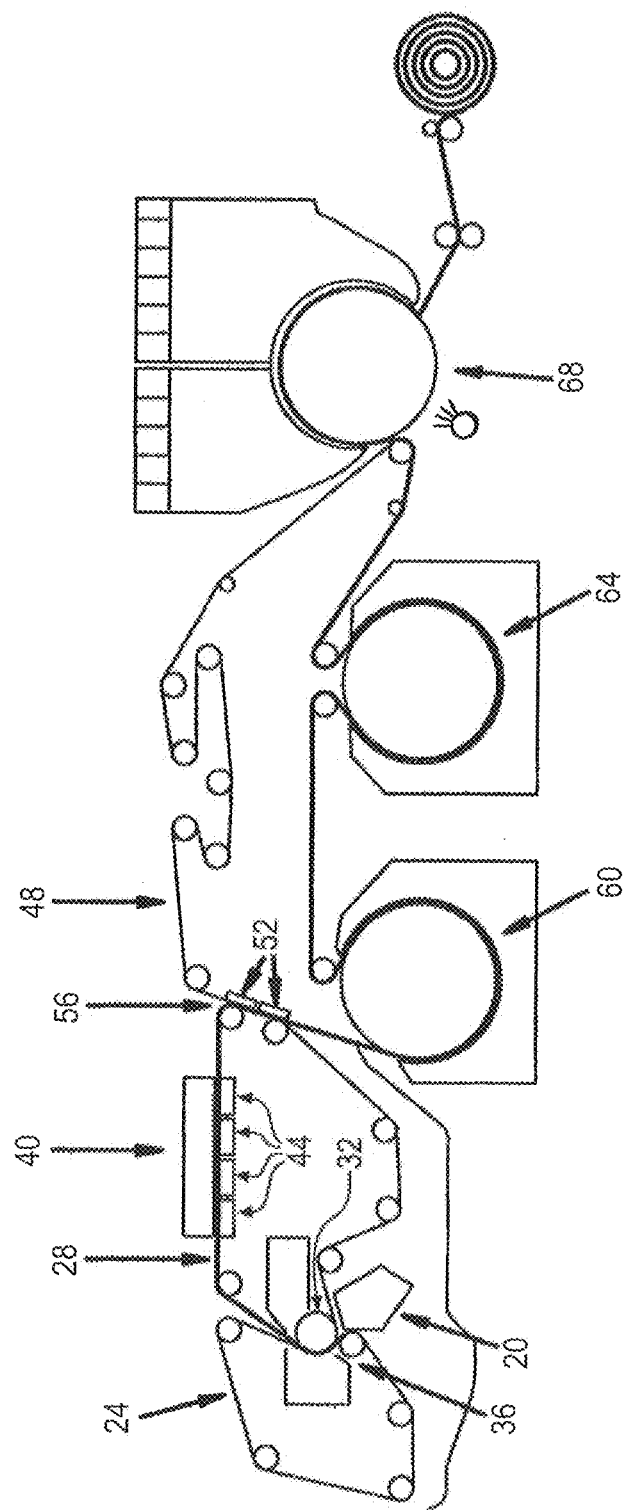
FIG. 1 is a schematic diagram of a paper machine that uses a structuring fabric.

FIG. 1 shows an example of a through air drying (TAD) papermaking process in which a structuring fabric 48 is used to form the three-dimensional structure of the paper product. To begin the process, furnish supplied through a head box 20 is directed in a jet into the nip formed between a forming fabric 24 and a transfer fabric 28. The forming fabric 24 and the transfer fabric pass between a forming roll 32 and a breast roll 36. The forming fabric 24 and transfer fabric 28 diverge after passing between forming roll 32 and breast roll 36. The transfer fabric 28 then passes through dewatering zone 40 in which suction boxes 44 remove moisture from the web and transfer fabric 28, thereby increasing the consistency of the web, for example, from about 10% to about 25% prior to transfer of the web to structuring fabric 48. In some instances, it will be advantageous to apply some amount of vacuum as indicated through vacuum assist boxes 52, in a transfer zone 56, particularly, when a considerable amount of fabric crepe is imparted to the web in transfer zone 56 by a rush transfer wherein the transfer fabric 28 is moving faster than the structuring fabric 48.

Because the web still has a high moisture content when it is transferred to the structuring fabric 48, the web is deformable such that portions of the web can be drawn into pockets formed between the yarns that make up the structuring fabric 48 (the formation pockets in a fabric will be described in detail below). As the structuring fabric 48 passes around the through dryers 60 and 64, the consistency of the web is increased, for example, to about 60% to about 90%. The web is thereby more or less permanently imparted with a shape by the structuring fabric 48 that includes domes where the web is drawn into the pockets of the structuring fabric 48. Thus, the structuring fabric 48 provides a three-dimensional shape to the web that results in a paper product having the dome structures.

To complete the paper forming process, the web is transferred from the structuring fabric 48 to the Yankee cylinder 68 without a major degradation of its properties by contacting the web with adhesive sprayed on to Yankee cylinder 68 just prior to contact with the translating web. After the web reaches a consistency of at least about 96%, light creping is used to dislodge the web from Yankee cylinder 68.

While FIG. 1 demonstrates one type of process in which a structuring fabric is used to impart a three-dimensional shape to a paper product, there are many other papermaking processes in which a structuring fabric can be used to impart a three-dimensional structure to the paper product. For example, a structuring fabric may be used in a papermaking process that does not utilize through air drying (TAD). An example of such a non-TAD process is disclosed in U.S. Pat. No. 7,494,563, the disclosure of which is incorporated by reference in its entirety. As will be appreciated by those skilled in the art, the invention disclosed herein is not limited to being used in any particular papermaking process, but rather, may be applied to fabrics used in a wide variety of papermaking processes.

Figure 2:
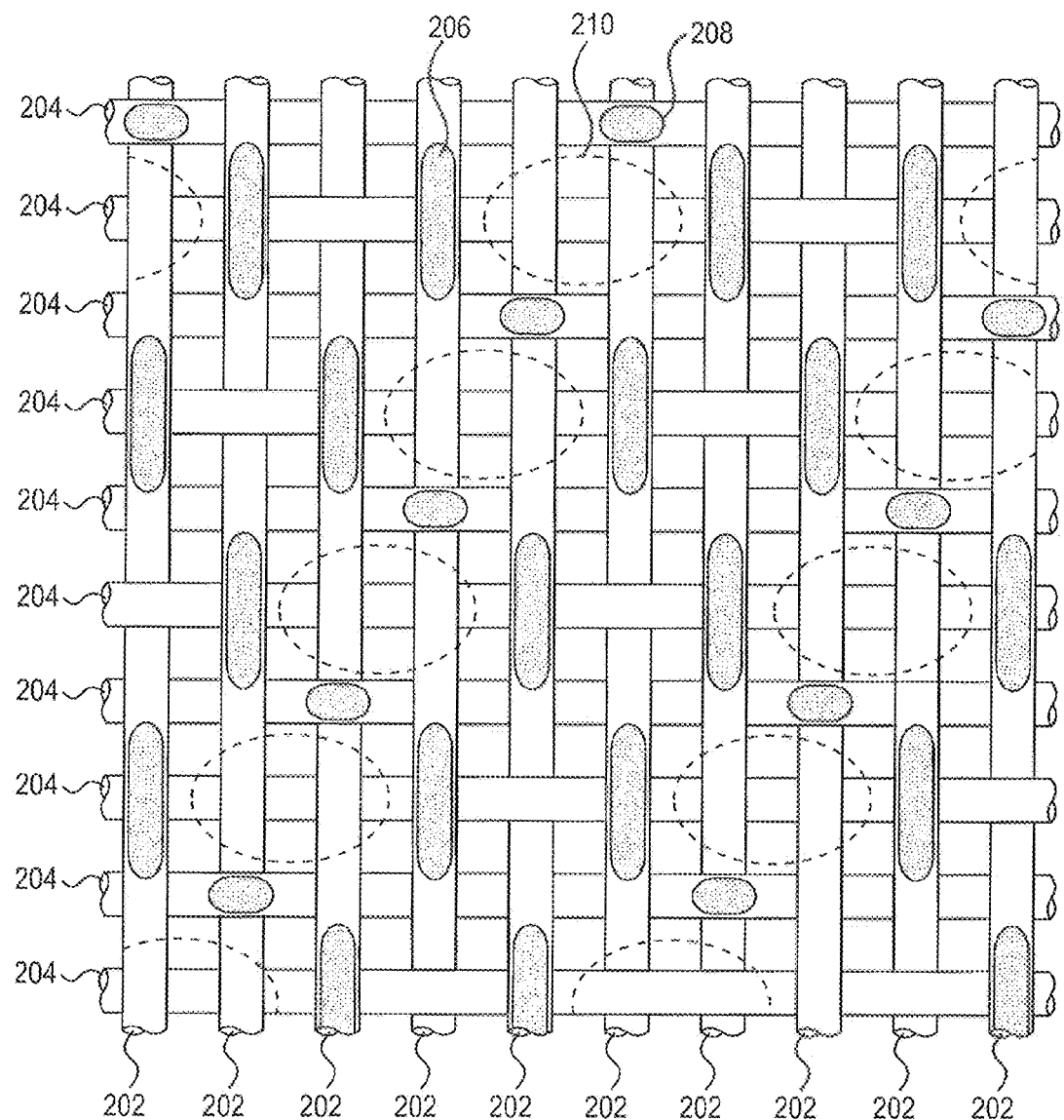
FIG. 2 is a top view of a section of a structuring fabric.

FIG. 2 is a view of a portion of the web facing side of a structuring fabric 200. The fabric 200 includes warp yarns 202 that would run in the machine direction (MD) when the fabric 200 is used in a papermaking process, and weft yarns 204 that run in the cross machine direction (CD) when the fabric 200 is used in a papermaking process. The warp and weft yarns 202 and 204 are weaved together so as to form the structure of fabric 200. It should be noted that, when looking down on FIG. 2, the web-contacting surface of the structuring fabric 200, some of the depicted yarns 202 and 204 are below the plane that contacts the web during the papermaking process, i.e., the contact surface of the fabric 200. The uppermost points of the yarns 202 and 204 that define the plane of the contact surface are the knuckles 206 and 208. That is, the knuckles 206 and 208 form the actual contact surface of the forming fabric 200. Pockets 210 (shown as the outlined areas in FIG. 2) are defined in the areas between knuckles 206 and 208. During a papermaking operation, portions of the web can be drawn into the pockets 210, and it is the portions of the web that are drawn into the pockets 210 that correspond to the domes in the finished paper product, as also described above.

It should be noted that a structuring fabric may not initially be manufactured with knuckles, such as the knuckles 206 and 208 in FIG. 2. Instead, knuckles are often formed by sanding or grinding one of the surfaces of the structuring fabric. Further, as the structuring fabric is used in a papermaking operation, wear on the surface of the structuring fabric may further increase the length of the knuckles. As will be described below, the present invention provides for determining characteristics of the knuckles, including characteristics of the knuckles as the fabric is subjected to wearing.

It should also be noted that a structuring fabric can take on numerous forms, depending on, for example, the weave pattern of the warp and weft yarns and the size of the yarns. The structuring fabric 200 depicted in FIG. 2 includes knuckles 206 that are formed on the warp yarns 202 and knuckles 208 that are formed on the weft yarns 204. This may have resulted from the fabric 200 being sanded or worn to the point that the knuckles are formed on both the warp and weft yarns 202 and 204. With less sanding, however, the fabric 200 might have only knuckles 206 on the warp yarns 202, and not on knuckles 208 on weft yarns 204, or vice versa. Numerous configurations of weft and warp yarns in structuring fabrics are known in the art, and the numerous configurations allow for differently shaped paper products to be formed with the fabrics.

Figure 3:
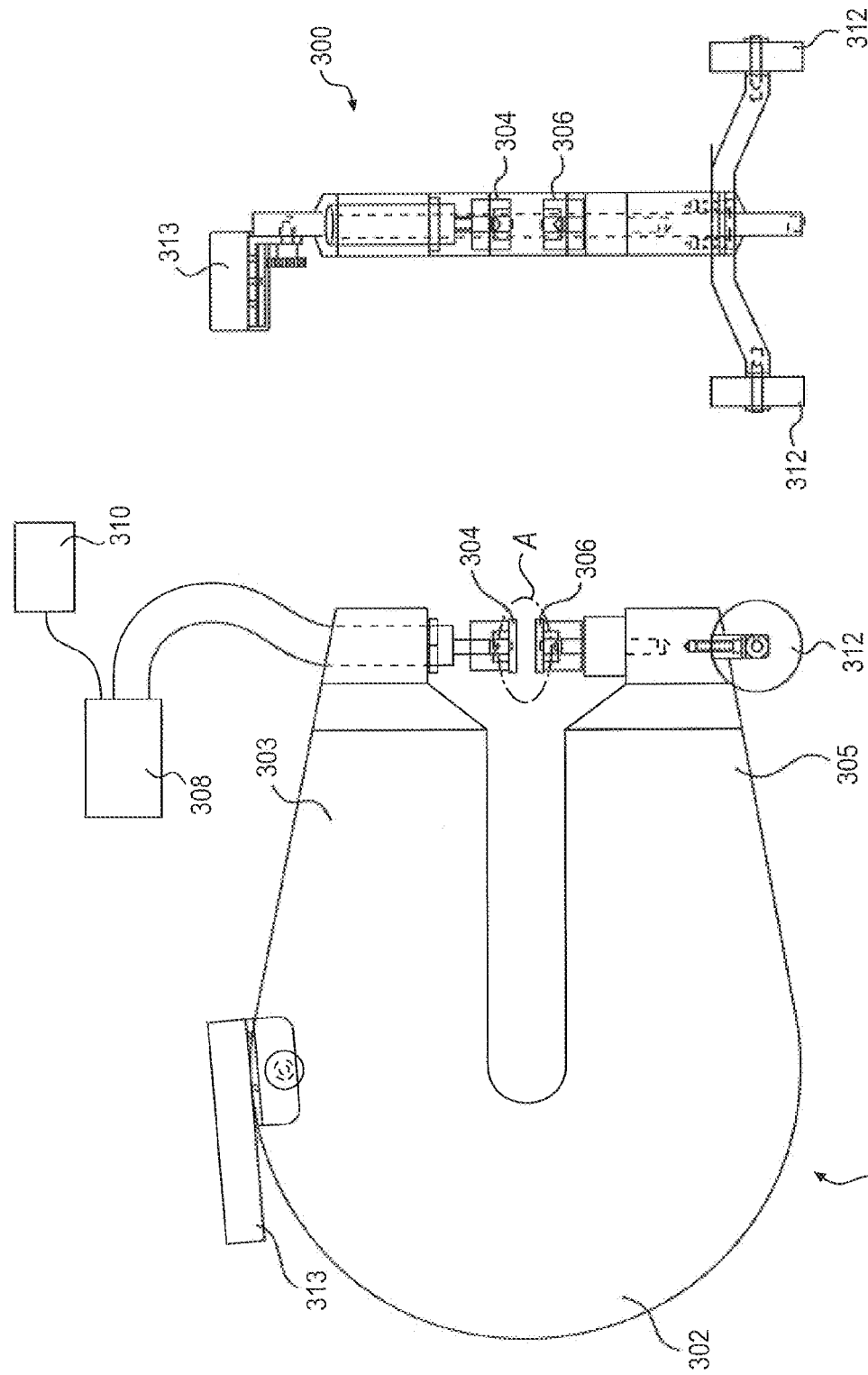
FIGS. 3A and 3B are views of contact surface printing apparatus according to the invention.

An apparatus and a technique for forming a print of the contact surface formed by the knuckles of a fabric is shown in FIGS. 3A and 3B. FIG. 3A is a side view of a contact surface printing apparatus 300, and FIG. 3B is a front view of the contact surface printing apparatus 300. This apparatus 300 includes a C-shaped frame structure 302 with first and second arms 303 and 305. A first plate 304 is movably supported by die first arm 303, and a stationary second plate 306 is supported by the second arm 305. A print of the knuckles of a fabric is formed between the first and second plates 304 and 306, as will be described in detail below.

The first plate 304 is operatively connected to a pump 308 for actuating movement of the first plate 304 towards the second plate 306. In some embodiments, the hand-operated hydraulic pump 308, with a release valve for allowing the first plate 304 to be retracted from the second plate 306. The pump 308, however, can take many other forms so as to effect movement of the first plate 304. The pump 308 may be connected to a transducer and transducer indicator 310 for measuring the pressure applied by the pump 308 to the first plate 304 as the first plate 304 is pressed against the second plate 306. As a specific example, an ENERPAC® Hydraulic Hand Pump Model CST-18381 by Actuant Corp. of Milwaukee, Wis., can be used. As a specific example of the pressure transducer, a Transducer Techniques Load Cell Model DSM-5K with a corresponding indicator, made by Transducer Techniques, Inc., of Temecula, Calif., can be used. Of course, in other embodiments, the pump 308 and transducer and transducer indicator 310 may be combined into a single unit.

The frame 302 of the contact surface printing apparatus 300 includes wheels 312 adjacent to the front end of the frame 302, as well as a mount 313 that may be used to hold the pump 308 and/or transducer 310. One or more wheels provided to the frame 312 make the frame 302 easier to move. An advantageous feature of the contact surface printing apparatus 300, according to embodiments of the invention, is its portability. For example, with a configuration as shown in FIGS. 3A and 3B, the print apparatus 300 may be easily moved about sections of a fabric that is mounted on a papermaking machine. As will certainly become appreciated by those skilled in the art, the ability to form prints of the contact surface of a fabric while the fabric is mounted to a papermaking machine, and, thus, characterize the fabric according to the techniques described below, provides numerous benefits. As but one example, the wearing of a fabric on a papermaking machine can easily be monitored by using the contact surface printing apparatus 300 so to take prints of the knuckles of the fabric after different periods of operation of the papermaking machine.

While the contact surface printing apparatus 300 shown in FIGS. 3A and 3B includes a frame structure 302 that connects the first and second plates 304 and 306, in other embodiments, a contact surface printing apparatus may not include such a single frame structure 302. Instead, the first and second plates 304 and 306 may be non-connected structures that are individually aligned to form the print of a fabric. In still other embodiments, the plates 304 and 306 may take vastly different forms from those depicted in FIGS. 3A and 3B. For example, one of the plates 304 and 306 could be formed as an extended surface, while the other plate is formed as a circular structure that is roiled across the extended surface. The term "plate," as used herein, is a broad term that encompasses any structure sufficient for contacting and/or supporting the components for making the print of the fabric. Additionally, as is clear from the description above, the relative motion of the first and second plates 304 and 306 in any embodiment could be reversed, such that the second plate 306 is made movable while the first plate 304 is held stationary.

Figure 4:
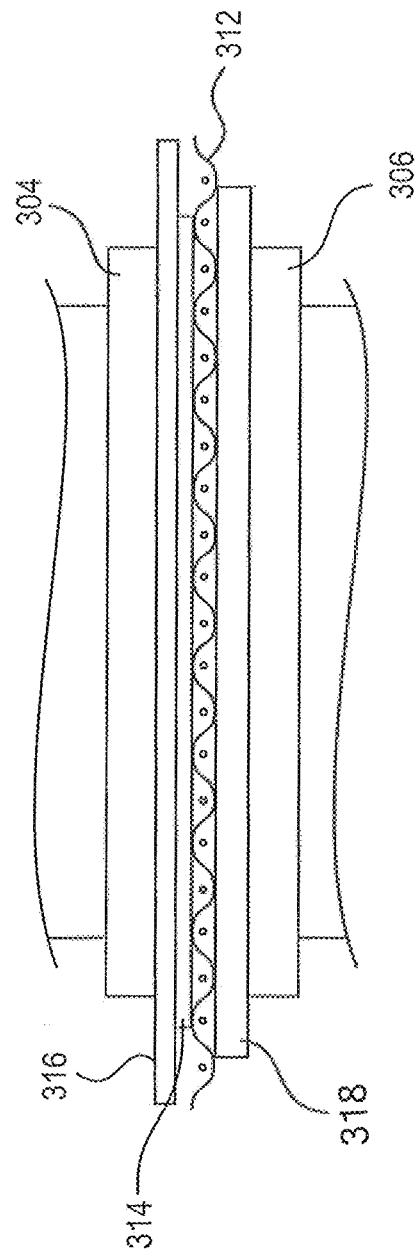
FIG. 4 is a detailed view of the pressing section of the print forming apparatus shown in FIGS. 3A and 3B.
Figure 5A:
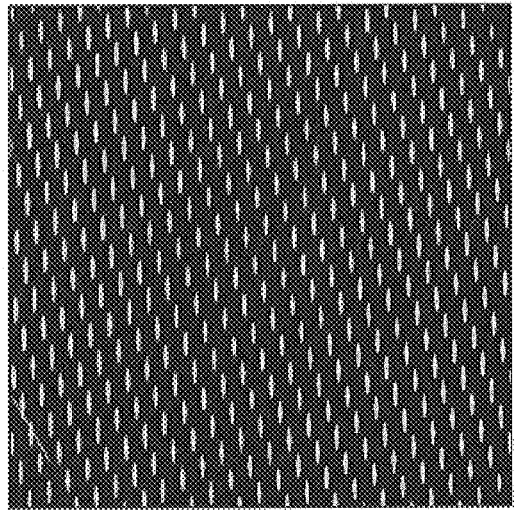
FIGS. 5A through 5D are examples of prints of structuring fabric made according to the invention.
Figure 5B:
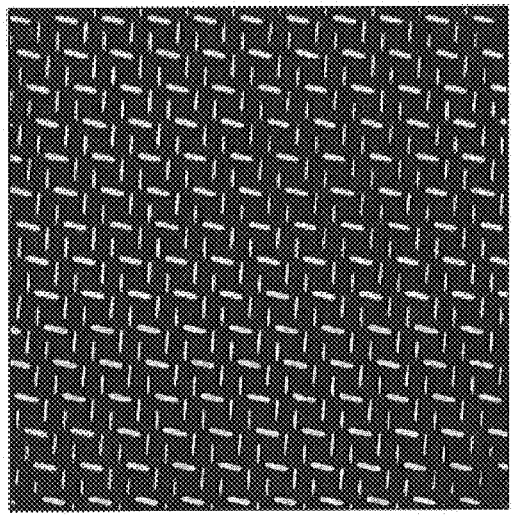
Figure 5C:
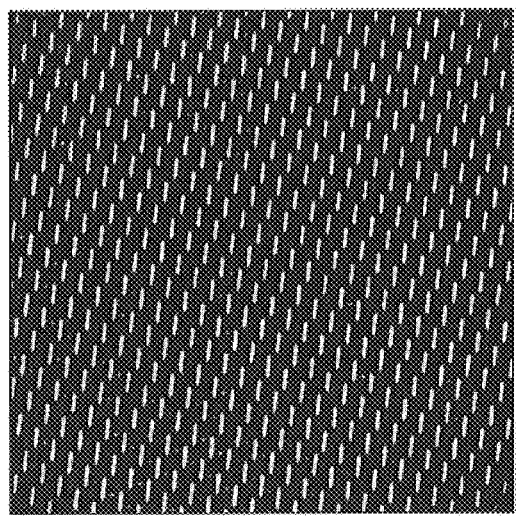
Figure 5D:
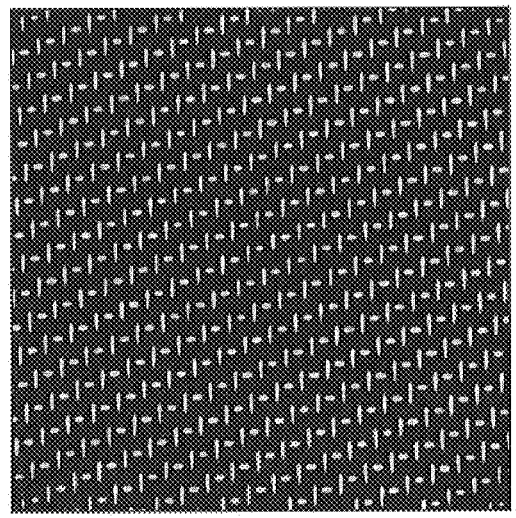

FIG. 4 is a detailed view of Section A of the contact surface printing apparatus 300 shown in FIG. 3A, with the apparatus 300 being set up to make a print of a section of a fabric 312. The fabric 312 is positioned between the plates 304 and 306, and a strip of pressure measurement film 314 is positioned against the structuring fabric 312. Between the pressure measurement film 314 and the first plate 304 is one or more sheets of paper 316. Between the fabric 312 and the second plate 306 is a strip of rubber 318.

Pressure measurement film is a material that, is structured such that the application of force upon the film causes microcapsules in the film to rupture, producing an instantaneous and permanent, high-resolution image in the contacted area of the film. An example of such a pressure measurement film is sold as Prescale film by Fujifilm Holdings Corporation of Tokyo, Japan. Another example of pressure measurement film is PRESSUREX-MICRO® by Sensor Products, Inc., of Madison, N.J. Those skilled in the art will recognize that other types of pressure measurement films could be used in the printing techniques described herein. In this regard, it should be noted that for the analysis techniques described below, the pressure measurement film need not provide an indication of the actual pressure applied by the fabric to the film, but rather, the pressure measurement film need only provide a print image showing the contact surface formed by the knuckles of a fabric.

The pressure applied to plate 304 when forming a print of fabric 310 on pressure measurement film 314 can be selected so as to simulate the pressure that would be applied to a web against the fabric 312 in an actual papermaking process. That is, the pump 308 may be used to generate a pressure (as measured by transducer 310) on the plate 304 that simulates the pressure that would be applied to a web against the fabric 312 in a papermaking process. In the papermaking process described above in conjunction with FIG. 1, the simulated pressure would be the pressure that is applied to the web against the fabric 48 to the Yankee cylinder 68. In some papermaking processes, such as the process described in aforementioned U.S. Pat. No. 7,494,563, the pressure applied to the web against the fabric is generally in the range of six hundred psi. Accordingly, to simulate this papermaking process, six hundred psi of pressure would be applied by the hydraulic pump 308 to the plate 304 when forming the image of the knuckles of fabric 312 in the pressure measurement film 314. For such an operation, it has been found that medium pressure 10-50 MPa Prescale film by FujiFilm can provide a good image of the knuckles of a structuring fabric.

Referring again to FIG. 4, the paper 316 acts as a cushion to improve the print of the fabric 312 formed on the pressure measurement film 314. That is, paper 316 provides compressibility and a smooth surface, such that the knuckles of the fabric 312 may "sink" into the pressure measurement film 314, which, in turn, forms a high resolution image of the knuckles in the film 314. To provide these properties, construction and kraft are examples of types of paper that could be used for the paper 316.

The strip of rubber 318 creates a level contact surface for supporting the fabric 314. In embodiments of the invention, the plates 304 and 306 are made of a metallic material, such as steel. A steel plate would most likely have imperfections that reduce the quality of the print of the knuckles of the fabric formed in the pressure measurement paper 316. The paper 316 and die rubber 318 that are used between the plates 304 and 306, and the pressure measurement film 314 and the fabric 312, however, provide more level contact surfaces than the surfaces of the metallic plates 304 and 306, thereby resulting in better images being formed in the pressure measurement film 314. Those skilled in the art will recognize that other materials in alternative to the paper 316 and rubber 318 may be used as structures to provide the level surfaces between the plates 304 and 306 of the apparatus 300.

In other embodiments, a print is made of the knuckles of a fabric in materials other than pressure measurement film. Another example of a material that can be used to form prints of a film is wax paper. A print of the contact surface of a fabric may be made in a wax surface by pressing the contact surface of a fabric against wax paper. The print in the wax paper could be made using the plates 304 and 306 in die print forming apparatus 300 described above, or with other configurations of the plates. The wax paper print can then be analyzed in the same manner as a pressure measurement film print, as will be described below.

FIGS. 5A through 5D show examples of prints of knuckles formed in pressure measurement film using the contact surface printing apparatus 300. In these prints, the distinctive shapes and patterns of the knuckles of the fabrics can be seen. As discussed above, the knuckles form the contact surface for the fabric. Hence, high resolution prints of the knuckles in a pressure measurement film, such as those shown in FIGS. 5A through 5D, provide an excellent representation of the contact surface of a Fabric.

Next, a system for analyzing the prints of knuckles, such as those shown in FIGS. 5A through 5D, will be described. In the system, graphical analysis will be conducted on a conventional computer system. Such a computer system will include well-known components, such as at least one computer processor (e.g., a central processing unit or a multiple processing unit) that is connected to a communication infrastructure (e.g. a communications bus, a cross-over bar device, or a network). A further component of the computer system is a display interface (or other output interface) that forwards video graphics, text, etc., for display on a display screen. The computer system may still further include such common components as a keyboard, a mouse device, a main memory, a hard disk drive, a removable-storage drive, a network interface, etc.

As a first step in the analysis, a print of the contact area of the knuckles of a fabric is converted to a computer readable image using a photoscanner. Any type of photoscanner may be used to generate the computer readable image. In certain embodiments, however, a photoscanner having at least 2400 dpi has been found to provide a good image for analysis. With the resolution of the scan of the image, an imaging analysis program (as will be described below) can apply an exact scale to the image. As will be described below, the exact scaling will be used in the calculation of the surface characteristics of the structuring fabric.

The scanned image may be stored in a non-transitory computer-readable medium in order to facilitate the analysis described below. A non-transitory computer readable medium, as used herein, comprises all computer-readable media except for a transitory, propagating signal. Examples of non-transitory computer readable media include, for example, a hard disk drive and/or a removable storage drive, representing a disk drive, a magnetic tape drive, an optical disk drive, etc.

The scanned image, as well as characteristics of the contact surface scanned image that are determined according to the techniques described below, may be associated with database. A. "database," as used herein, means a collection of data organized in such a way that a computer program may quickly select desired pieces of the data, e.g. an electronic filing system. In some implementations, the term "database" may be used as shorthand for "database management system."

In order to perform quantitative analysis of the scanned print image, an image analysis program is used with the scanned images of the knuckles of a fabric. Such an image analysis program is developed, for example, with computational software that works with graphical images. One example of such computational development software is MATHMATICA® by Wolfram Research, LLC, of Champaign, Ill. As will be described below, the image analysis program will be used to specifically identify the knuckles in the fabric print image of the structuring fabric, and, with known scaling of the fabric print image, the image analysis program can calculate the sizes of the knuckles and estimate sizes of the pockets.

When analyzing the scanned image, any size area that includes a plurality of knuckles and a pocket could be used for the analysis described below. In specific embodiments, it has been found that a 1.25 inch by 1.25 inch area of an image of a fabric allows for a good estimation of properties, such as pocket sizes using the techniques described herein. In particular, it has been found that when an image is formed with a 2400 dpi resolution (discussed above), and using a 1.25 inch by 1.25 inch area of an image for the analysis, a good characterization of the contact surface can be conducted. Of course, other resolutions and/or area may also provide good results.

Figure 6A:
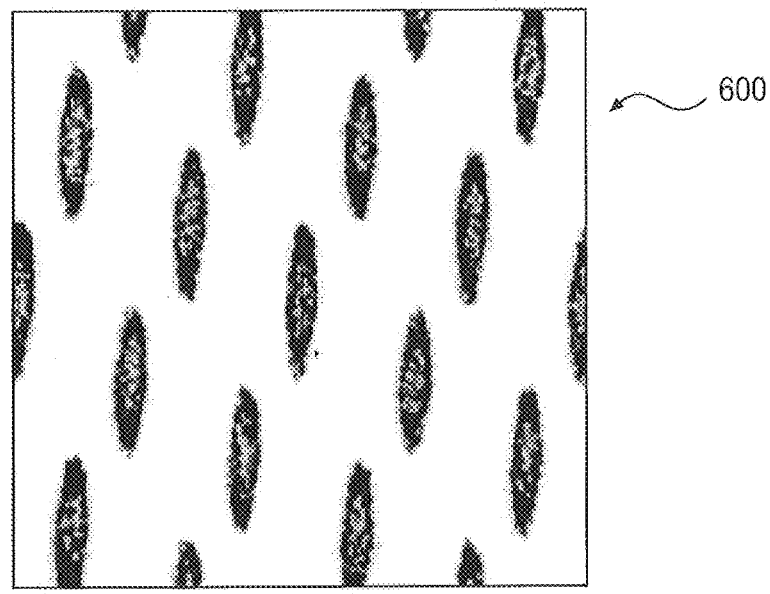
FIGS. 6A through 6E show the steps of establishing a coordinate system for the structuring fabric print.

FIG. 6A through 6E depict the steps of identifying the knuckles in a magnified portion of the scanned image of a print using the image analysis program. Initially, as shown in FIG. 6A, a magnified portion of an image 600 is viewed on the display screen of the computer system running the analysis program. The image 602, which may be formed using the print technique described above, shows the knuckles 602. Along with using the image 600 with the analysis program, the scaling of the image 600 can be input into an analysis program. Such a scaling may be input, for example, as 2400 dpi, from which the analysis program can apply the scale SC to the image 600, fire analysis program will then use the scale to calculate the sizes and positions of the knuckles, as described below.

Figure 6B:
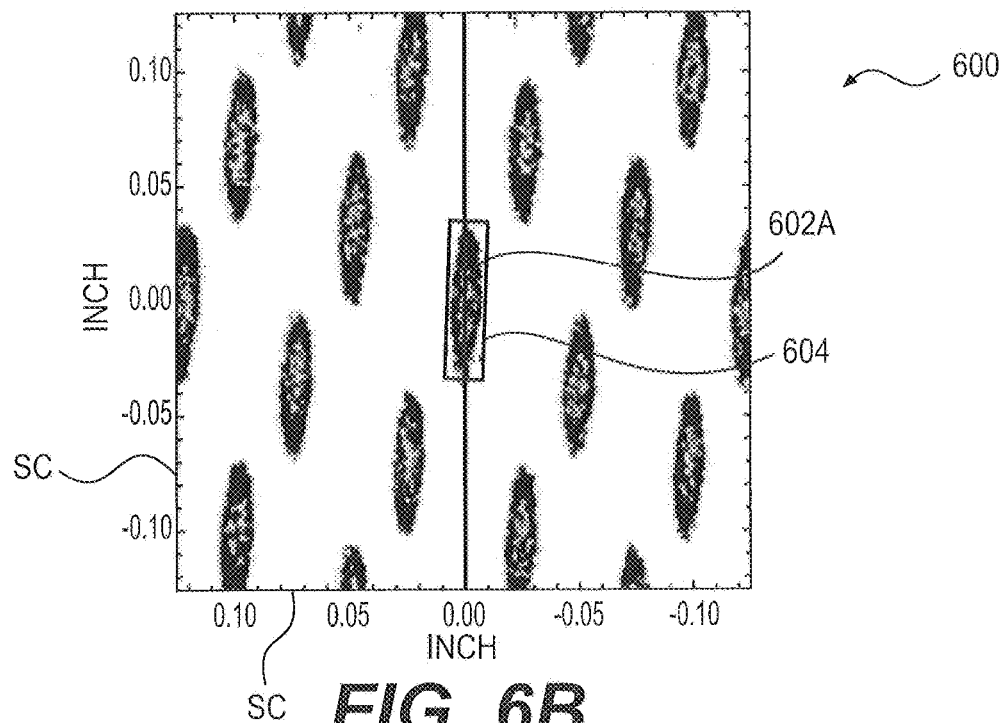
Figure 6C:
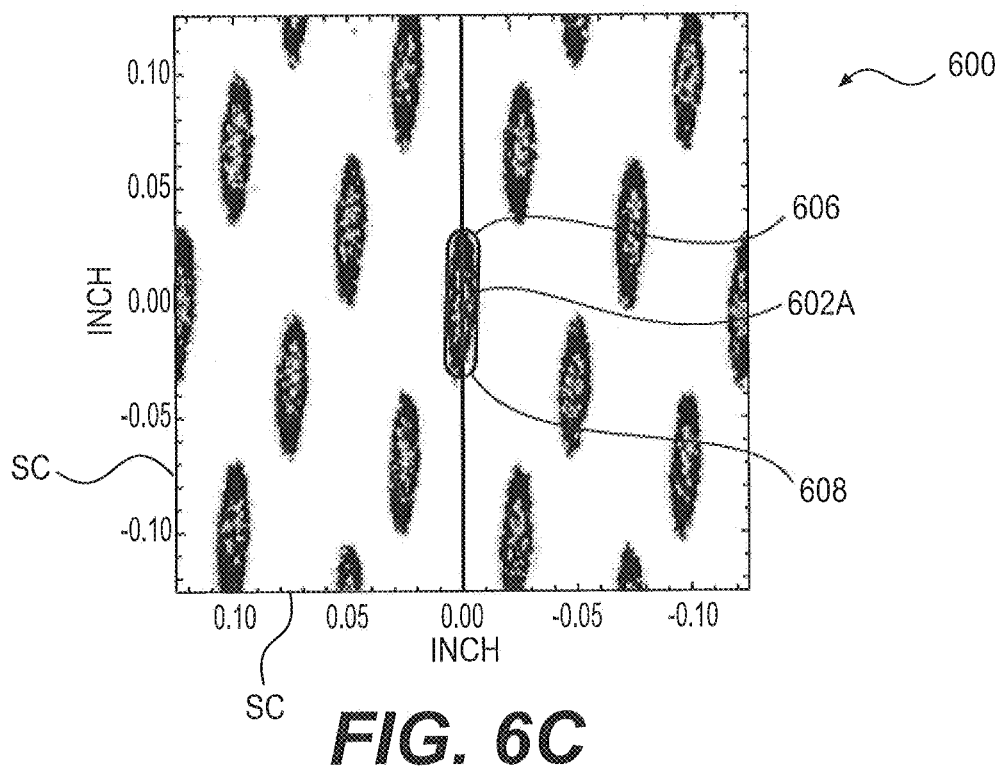

FIGS. 6B and 6C shows steps for identifying a specific knuckle 602A using the analysis program. The knuckle 602A is initially selected based on its location at a center region of the magnified image 600. In this step, a rough outline of the knuckle 602A is applied. The rectangular box 604, which may be a stored shape in the analysis program, is initially applied around the knuckle 602A in order to initiate the knuckle identification process. The initial rectangular box 604 shape may then be more closely refined to match the shape of the knuckle 602A, as shown in FIG. 6C. In this case, the ends 606 and 608 are reshaped to be more rounded, and, thus, more closely correspond to the ends of the knuckle 602A. Although not shown, further refinements could be made to the outline of the knuckle 602A until a sufficient match is made. Such refinements might be conducted by further magnifying the image 600.

Figure 6D:
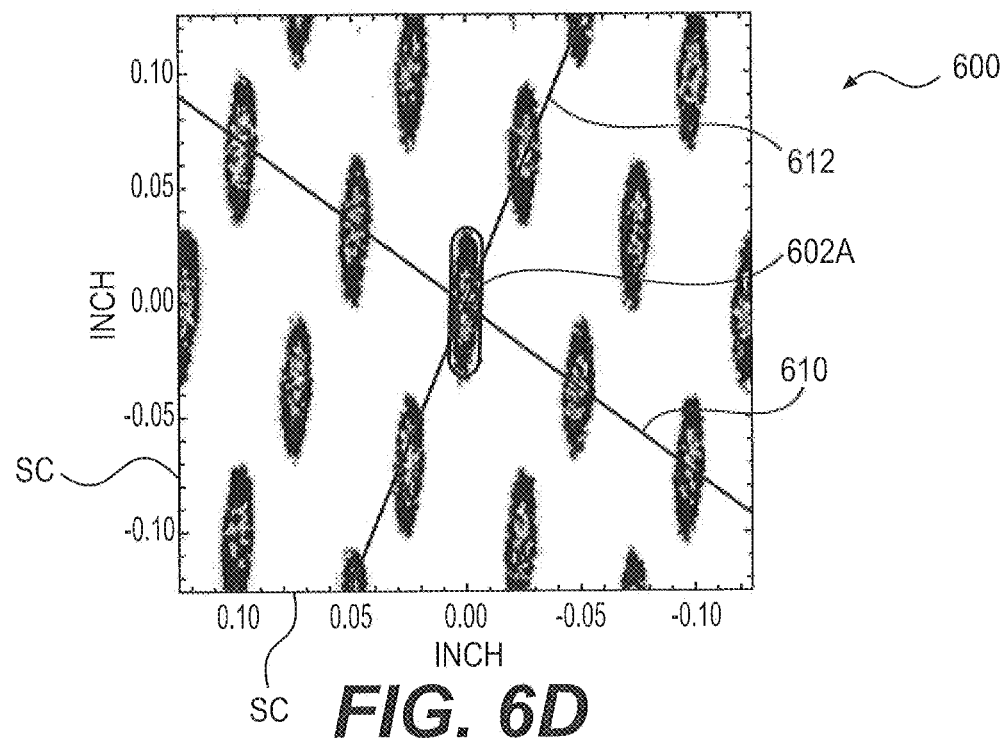

As shown in FIG. 6D, after the knuckle 602A is identified by the outline, guidelines 610 and 612 are drawn. The guidelines 610 and 612 are each drawn so as to pass through the center of the knuckle 602A, and extend in straight lines through the centers of the other knuckles. Notably, the guidelines 610 and 612 are also drawn so as to not cross the areas where pockets are formed in the fabric, which are known to correspond to the areas between groups of knuckles. By drawing the guidelines 610 and 612 straight between the centers of the knuckles, the guidelines 610 and 612 do not cross the area of the pockets that are formed between the knuckles.

Figure 6E:
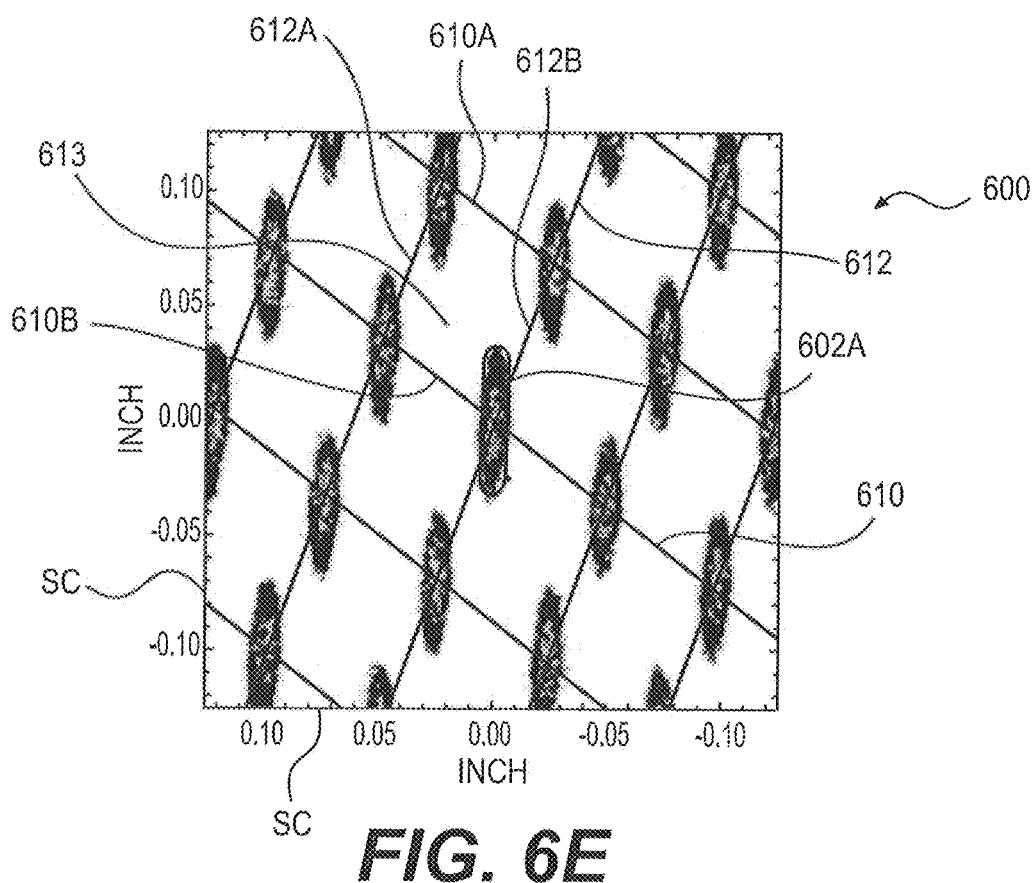

After the guidelines 610 and 612 are drawn, as shown in FIG. 6E, further guidelines are drawn. These guidelines are drawn in a similar manner to guidelines 610 and 612, i.e., through the centers of the knuckles and not passing through areas where pockets are formed. To aid in the process of drawing the guidelines, a lower magnification may be used. With the guidelines, a coordinate system is, in effect, established for the positions of the knuckles. The analysis program, therefore, can now identify the size and shape of the knuckles based on the outline 602A, and can identify the locations of the knuckles as determined by the points wherein the guidelines cross. The analysis program further has the input the scale SC of the image 600. It follows that the analysis program can apply the scale to the outline knuckle 602A and the knuckle positioning to calculate the actual sizes and spacing of the knuckles. Note as well that the analysis program may calculate the frequency of the guidelines such as the number of times that the guidelines 612 cross guideline 610 per a unit length. The frequency of the each set of guidelines 610 and 612 will be used in calculations of properties of the fabric, and in other aspects of the invention, as will be described below.

It should be noted that, as shown in FIGS. 6D and 6E, the knuckles are all about the same size and all about the same shape, and the knuckles are regularly spaced along the guidelines. This is not surprising inasmuch as most fabrics for papermaking machines are manufactured with highly consistent yarn patterns, which results in very consistent knuckle sizes and positions. The consistency in size, shape, and placement of the knuckles allows for accurate estimates of the size and shapes of all the knuckles on the contact surface of a fabric based on a single selected knuckle, or on a limited number of identified knuckles, and a close estimate of the sizes and locations of the knuckles can be achieved without identifying each knuckle. Of course, to achieve even further accuracy, more than one knuckle could be identified, and the outlines and guidelines could be drawn at different portions of an image.

As shown in FIG. 6E, the guidelines 610 and 612 define a plurality of unit cells. A particular unit cell 613 is shown between guideline segments 610A, 610B, 612A, and 612B. The unit cell 613, in effect, demonstrates die minimum repeating pattern in the fabric, and the maximum allowable pocket size. It should be noted while the fabric shown in FIGS. 6A through 6E has about one warp knuckle per unit cell, other fabrics may have more than one warp knuckle and/or more than one weft knuckle per unit cell. In other words, the unit cells defined by knuckle patterns will vary with different fabric patterns.

As will be readily apparent to those skilled in the art, any or all of the steps shown in FIGS. 6A through 6E can either be performed by a user on a display screen, or alternatively, may be automated so as to be performed upon execution of the analysis program. That is, the analysis program may be configured to automatically identify knuckles as the darkened regions of images, outline the knuckles, and then draw the guidelines based on the identified knuckles in the manner described above.

After the selected knuckle has been identified, and after the guidelines established through the knuckles, multiple properties of the fabric may be calculated using knuckle sizes and positions determined by the analysis program. To perform such calculations, the knuckle size and positioning data can be exported from the analysis program to a conventional spreadsheet program to calculate the properties of the fabric. Examples of the determinations made by the analysis program and the calculations that follow from such determinations are shown in Table 1.

TABLE 1

| Characteristic of the Fabric | Determination/Calculation |
|---|---|
| Knuckle Length (KL) | determined based on outline of identified warp knuckle or identified weft knuckle |
| Knuckle Width (KW) | determined based on outline of identified warp knuckle or identified weft knuckle |
| Frequency of Guidelines (f) | determined based on guidelines drawn through knuckles<br>freq 1 = frequency of one set of parallel lines (per inch or cm)<br>freq 2 = frequency of another set of parallel lines (per inch or cm) |
| Rounding Radius (r) | determined based on outline of identified warp knuckle and/or identified weft knuckle, the rounding radius is the level of rounding that is application to the corners of rectangular objects |
| Knuckle Density Per Unit Cell (KDUC) (knuckles per unit cell) | determined based on the number of warp or weft knuckles identified within a cell |
| Unit Cell Knuckle Area - (UKA) | warp UKA = warp KW × warp LW − ((2 × warp r)$^2$ − π(warp r)$^2$)<br>weft UKA = weft KW × weft LW − ((2 × weft r)$^2$ − π(weft r)$^2$) |
| Knuckle Density (KD) | F = freq 1 × freq 2<br>warp KD = F × warp KDUC<br>weft KD = F × weft KDUC |
| Total Warp or Weft Knuckle Contact Area (%) | warp area % = warp KD × warp UA<br>weft area % = weft KD × weft UA |
| Total % In-Plane Knuckle Contact Area (TKCA) | TKCA = warp area % + weft area % |
| % Area Contribution (AC) | % warp AC = [warp UA/(warp UA + weft UA)] × 100<br>% weft AC = [weft UA/(warp UA + weft UA)] × 100 |
| Pocket Area Estimate (PA) | PA = (1/(freq 1 × freq 2)) − (warp UA × warp KDUC) − (weft UKA × weft KDUC) |
| Pocket Density (PD) (pockets per square inch or centimeter) | PD = freq 1 × freq 2 |

The fabric from which image 600 was obtained only included knuckles 602 on the warp threads. Other fabrics, however, may include knuckles on the weft threads, such as the fabrics that formed the prints in FIGS. 5B and 5D. With such fabrics, the knuckles on the weft threads can be identified using the outlining technique described above, and the guidelines can be drawn through the weft knuckles using the technique described above.

While the contact surface of a fabric may be characterized by using a print of the knuckles of the fabric that is formed, for example, by the contact surface printing apparatus 300, in other embodiments, an image of the contact surface of the fabric may be obtained in a different manner. An alternative to forming a print of the knuckles of the fabric is to photograph the knuckles of a fabric, and then use the above-described procedures and techniques for analyzing an image formed from the photograph. In this regard, a photograph with 2400 dpi has been found to provide sufficient high and low resolution so as to be analyzed by the techniques described herein.

Figure 7A:
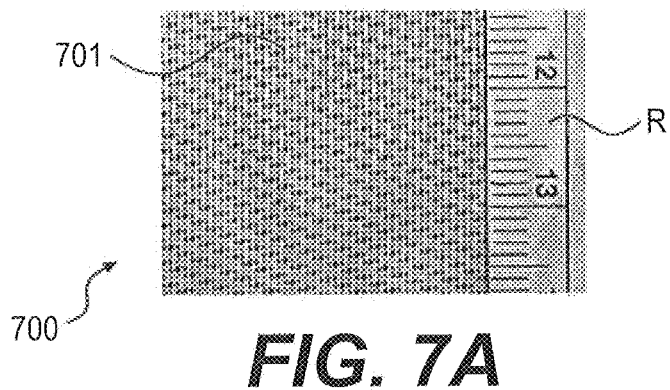
FIGS. 7A, 7B, and 7C show the application of the analytic technique herein applied to a photograph of the knuckles of a fabric.
Figure 7B:
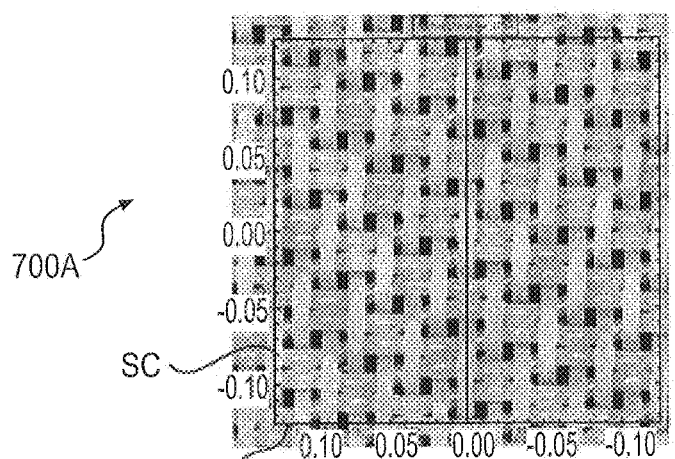
Figure 7C:
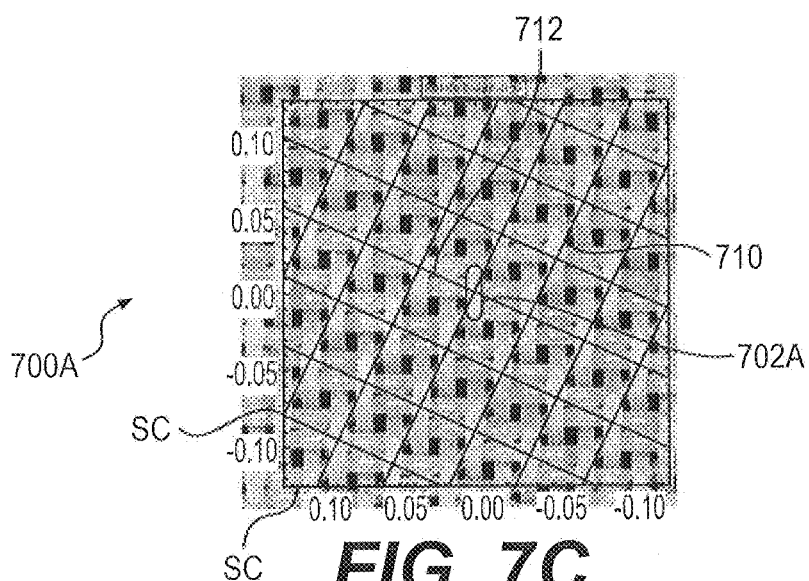

An example of a photograph 700 of the portion of a papermaking fabric with knuckles 702a is shown in FIG. 7A, and the application of the analytic above-described technique to the image generated from photograph 700 is shown in FIGS. 7B and 7C. The photograph 700 in FIG. 7A shows the fabric 701 next to a ruler R. When the photograph, is converted to an image for use with the analysis program, the scale for the image 700A can be input based on the photographed ruler R. That is, ruler R in the image 700A provides an input from which the analysis can apply a scale to the image. The displayed image 700A, along with die scale SC, is shown in FIG. 7B.

To identify the sizes and locations of knuckles in an image obtained from a photograph of the fabric, the same techniques described above with an image from a print of the fabric, may be used. For example, an outlined knuckle 702A and guidelines 710 and 712 are shown on the image 700A in FIG. 7C. With the knuckle sizing and location data from the analysis program, all of the above-described calculations may be carried out to characterize the contact surface of the fabric 700 that was photographed.

Table 2 below shows the results of the calculations of surface characteristics for a fabric, with one set of calculations being derived from a print of the fabric, and a second set calculations being derived from a photograph of the fabric.

TABLE 2

|  |  | Print of fabric | Photograph of fabric |
|---|---|---|---|
| Warp Knuckles | Contact Length (mm) | 1.27 | 1.27 |
|  | Contact Width (mm) | 0.28 | 0.28 |
|  | Percent Warp Contact | 19.9 | 20.5 |
| Weft Knuckles | Contact Length (mm) | 0.58 | 0.58 |
|  | Contact Width (mm) | 0.38 | 0.38 |
|  | Percent Weft Area | 11.2 | 11.5 |
| Total In-Plane Contact | Total Contact Area | 31.1 | 32.0 |
| Percent Warp-Weft Ratio | Warp Area (%) | 64 | 64 |
|  | Weft Area (%) | 36 | 36 |
| Pocket Density | (1/cm$^2$) | 58.4 | 60.2 |
| Fabric Cell Definition | Freq. 1 (1/cm) | 7.7 | 7.7 |
|  | Freq. 2 (1/cm) | 7.6 | 7.8 |

The results shown in Table 2 demonstrate that the contact surface characterization calculations achieved using the photograph technique closely correspond to the calculations achieved using the print of the fabric.

Another important characteristic of a papermaking fabric is the depth to which the web can be drawn into pockets in the fabric during the papermaking process. As discussed above, domes are formed in final paper products that correspond to the portions of the web that were drawn into the pockets in the fabric. Hence, the pocket depth of a papermaking fabric directly affects the paper product formed using the fabric. Techniques for determining the pocket depth of a fabric will now be described.

Figure 8:
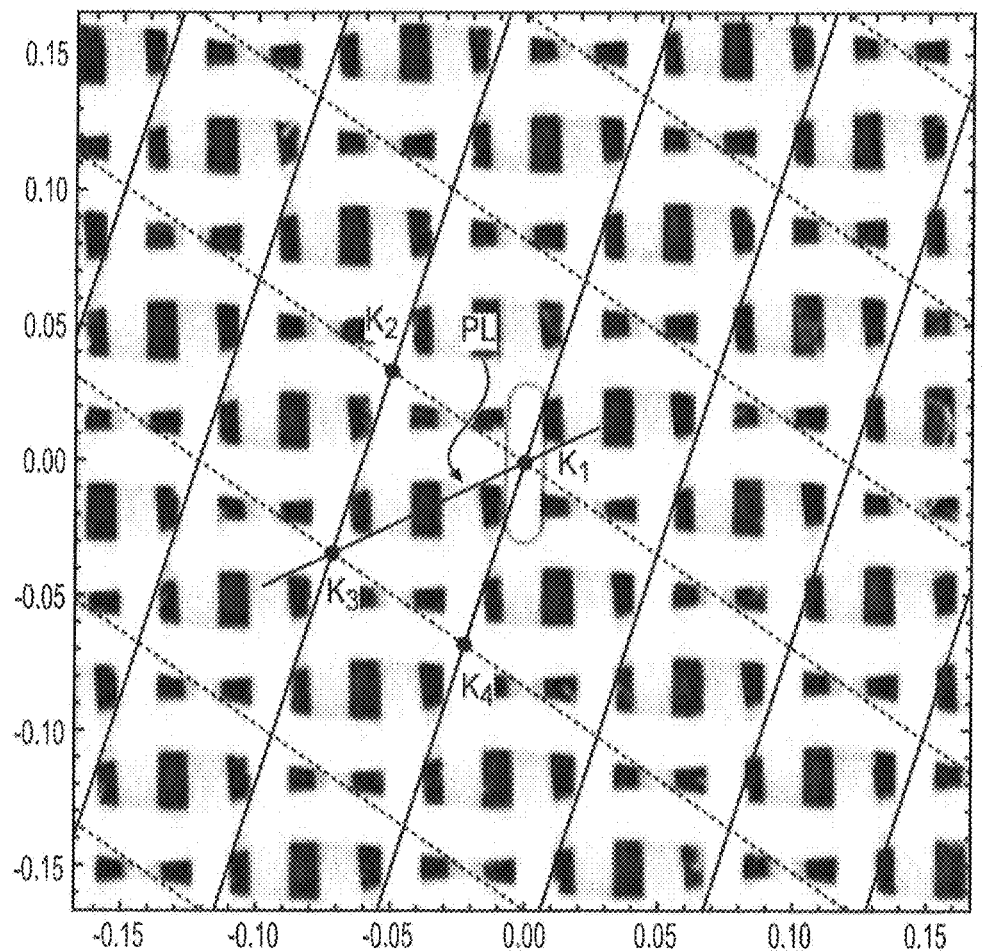
FIG. 8 shows the application of the analytic technique to determine a pocket surrounded by knuckles in a structuring fabric.

FIG. 8 shows a magnified photograph of a structuring fabric. With the photograph, and using the image analysis program described above, four knuckles K1 to K4 are identified. A parallelogram has been drawn in a manner that connects the knuckles K1 to K4, with the lines of the parallelogram being drawn to not pass through the pocket area that is formed between the knuckles K1 to K4. With the parallelogram drawn, a profile direction Line PL can be drawn that passes from the knuckle K1, through the center of the pocket, to knuckle K3. The profile direction line PL will be used to determine the pocket depth using a depth measurement instrument, as described below. Note that the profile direction line PL from knuckle K1 and knuckle K3 passes through the center of the pocket. As will be described below, the pocket depth of a structuring fabric is determined as the depth in the pocket to which the cellulosic fibers could penetrate in the paper making process. In the case of the fabric shown in FIG. 8, the maximum fiber migration depth is at the center of the pocket. It follows that a profile direction line could alternatively be drawn from knuckle K2 to knuckle K4 passing through the center of the pocket, and the alternative profile direction line could be used for the pocket depth determination described below. Those skilled in the art will also recognize that different structuring fabrics will have different configurations of knuckles and pockets, but a profile direction line could easily be determined for different structuring fabrics in the same manner as the profile direction line is determined as shown in FIG. 8.

Figure 9:
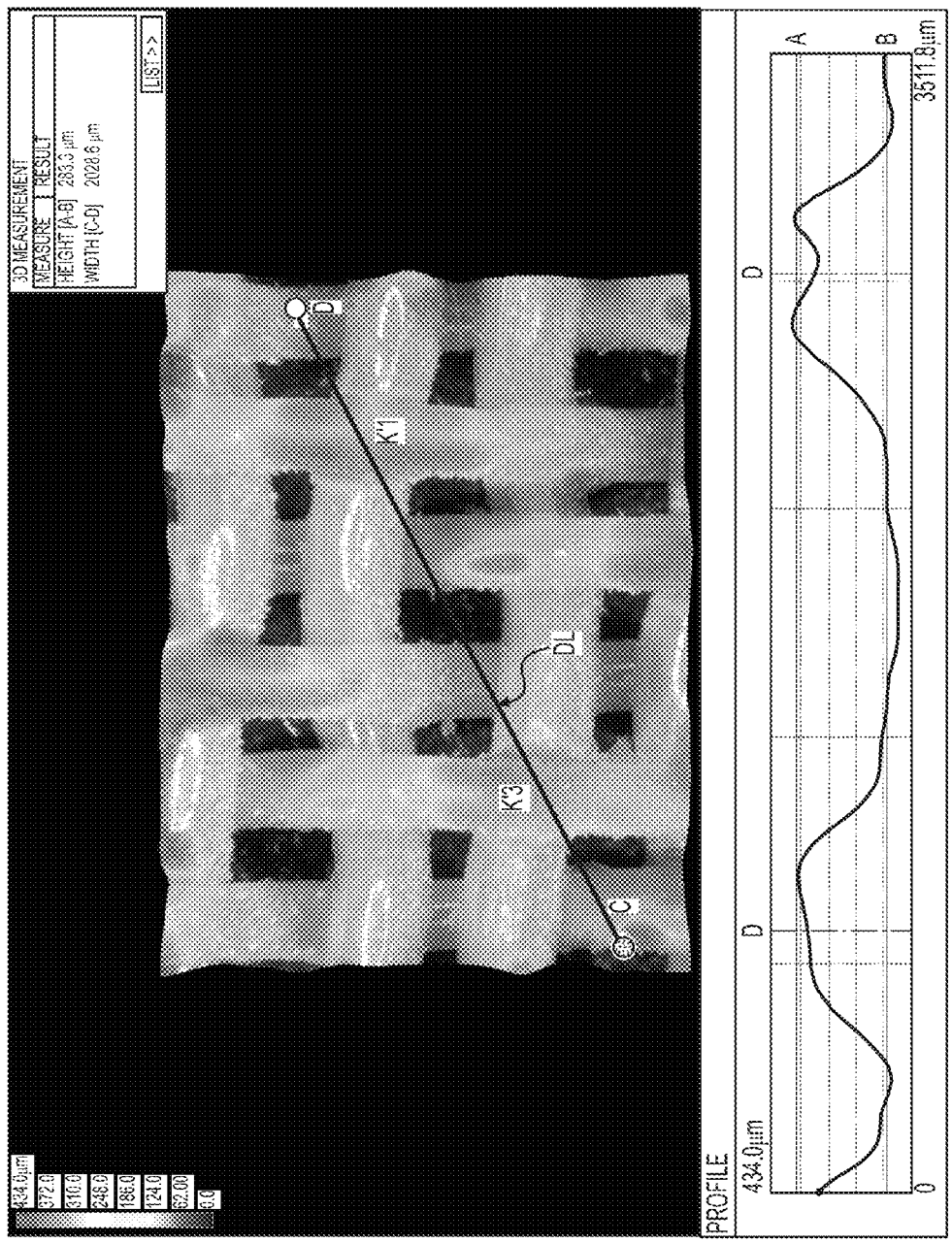
FIG. 9 shows the application of the analytic technique to determine the depth of the pocket shown in FIG. 8.

FIG. 9 is screenshot of a program used to determine the profile of a pocket of the structuring fabric shown in FIG. 8. The screenshot was formed using a VHX-1000 Digital Microscope manufactured by Keyence Corporation of Osaka, Japan. The microscope was equipped with VHX-H3M application software, also provided by Keyence Corporation. The microscopic image of the pocket is shown in the top portion of FIG. 9. In this image, the knuckles K'1 and K'3 and the pocket between the knuckles can easily be seen. A depth determination line DL has been drawn from point D to point C, with the depth determination line DL passing through the knuckles K'1 and K'3 and through the center of the pocket. The depth determination line DL is drawn to closely approximate the profile determination line PL that is shown in FIG. 8. That is, based on inspection of the depth determination line DL derived using the knuckle and pocket image shown in FIG. 8, a user can draw the depth determination line DL in the microscopic image shown in FIG. 9, with the depth determination line DL passing through the areas that correspond to the knuckles K'3 and K'1 and the center portion of the pocket.

With the depth determination line DL drawn, the digital microscope can then be instructed to calculate the depth profile of the pocket along the depth determination line DL, as is shown in the bottom, portion of FIG. 9. The profile of the pocket is highest at the areas corresponding to the knuckles K'3 and K'1, and the profile falls to its lowest point at the center of the pocket. The pocket depth is determined from this profile as starting from the height of the knuckles K'3 and K'1, which is marked by the line A on the depth profile. As with any two knuckles of a structuring fabric measured to this degree of precision, the knuckles K'3 and K'1 do not have the exact same height. Accordingly, the height A is determined as an average between the two heights of the knuckles K'3 and K'1, The pocket depth is determined as ending at a point just above the lowest point of die depth profile, marked by the line B on the depth profile. As those skilled in the art will appreciate, the depth of the pocket from line A to line B approximately corresponds to the depth in the pocket to which the cellulosic fibers in the web can migrate in a papermaking process. Note that the VHX-H3M software (discussed above) forms the full depth profile from a plurality of slices in the thickness direction of the fabric. Also, note that in forming the depth profile, the VHX-H3M software employs a filtering function to smooth the depth profile formed from the thickness slices. It should be noted that the measured pocket depth will slightly vary from pocket to pocket in a fabric. We have found, however, that an average of five measured pocket depths for a structuring fabric provides a good characterization of the pocket depth.

While a digital microscope is used in the above-described embodiments to determine the pocket depth, other instruments may alternatively be used to determine pocket depth with the techniques described herein. For example, in other embodiments, a laser profilometer (or "laser profiler") may be used to determine pocket depth in a similar manner as the above-described digital microscope. A laser profiler can determine a depth profile of a pocket that can be used to determine the pocket depth in the same manner as the depth profile generated using the digital microscope is used to determine pocket depth, as described above. An example of such a laser profiler is a TALYSURF® CLI high-resolution 3D surface profiling system manufactured by Taylor Hobson, Ltd. of Leicester, United Kingdom. In still other embodiments, an inline laser profile measurement device ("laser line scanner") may be used to determine the pocket depth of a fabric with the techniques described, herein. An example of such a laser line scanner is an LJ-V7000 series high-speed inline profile inspection device manufactured by Keyence Corporation.

When using a laser profiler or a laser line scanner, the same steps for determining the pocket depth may be used as are described above in conjunction with a digital microscope. That is, as shown in FIG. 8, the knuckles and a pocket are determined based on a representation of the surface of a structuring fabric. The laser profiler or laser line scanner is then set to determine a depth profile across the pocket front one knuckle to another knuckle, i.e., the laser profiler or laser line scanner scans across the line oriented as the line PL in FIG. 8. From this measured profile, the pocket depth can be determined in an analogous manner to that method described above in conjunction with FIG. 9. For performing analysis of the depth profile measured by the laser profiler or laser scanner, various analytic software programs may be used. One example is surface metrology software provided by TrueGage of North Huntingdon, Pa.

Each of the alternative depth measurement instruments, i.e. digital microscope, laser profiler, or laser line scanner, may offer certain advantages. For example, a digital microscope might provide a highly precise measurement of pocket depth. On the other hand, a laser profiler is generally an easy instrument to work with, and thereby can provide a quick measurement of pocket depth. As another example, a laser line scanner has the ability to quickly collect large volumes of data, and, thus, measure many depth profiles in a short period of time. In this regard, an embodiment of my invention includes using a laser line scanner to determine pocket depth profiles of a structuring fabric that is running on a papermaking machine. In this embodiment, the laser line scanner is positioned adjacent to the structuring fabric on the machine, with the laser line seamier measuring the pocket depth profiles as the fabric travels past the scanner. As will be appreciated by those skilled in the art, a structuring fabric in a papermaking machine may travel at speeds greater than 3,000 feet per minute. Yet, a laser line scanner, such as the aforementioned LJ-V7000 series inspection system by Keyance Corporation, has the ability to measure thousands of depth profiles per second. Accordingly, a laser line scanner has the ability to measure the pocket depth in the quickly moving structuring fabric, thereby providing highly useful pocket depth data while the structuring fabric is in actual use on a papermaking machine.

It should be noted that, regardless of the measurement instruments and technique used to determine pocket depth, the measured pocket depth will slightly vary from pocket to pocket in a fabric. I have found that, generally speaking, an average of five measured pocket depths for a structuring fabric provides a good characterization of the pocket depth. Of course, more or fewer measure measurements can be performed to determine an average pocket depth depending, for example, on the level of accuracy desired in the measurement.

In the pocket depth determination techniques described above, the structuring fabric itself is used to determine the pocket depth. In some cases, it may be easier to form a representation of the fabric, and then determine the pocket depth from the representation. For example, a representation of the knuckle and pocket structure of a fabric can be formed by pressing the contact surface of a fabric against wax paper, as is also described above. The wax representation of the fabric can then be scanned using one of the above-described techniques, for example, a laser line scanner can be used to determine the depth in the wax print between the knuckles in the wax print.

Those skilled in the art will recognize that the effective volume of the pockets of a structuring fabric is an important property of a structuring fabric that can easily be determined once the pocket size is calculated according to one of the above-described techniques. The effective volume of a pocket is the product of the cross-sectional area of the pocket at the surface of the structuring fabric (i.e., between the knuckle surfaces) multiplied by the depth of the pocket into which cellulosic fibers in the web can migrate during the papermaking process. The cross-sectional area of the pockets is the same as the estimate of the pocket area (PA), as described in TABLE 1 above. Thus, the effective pocket volume may be calculated simply as the product of the pocket area estimate and the measured pocket depth.

Another important property of a structuring fabric may be defined as a planar volumetric index for the fabric. Generally speaking, the softness, absorbency, and caliper of paper products made using a fabric may be influenced by the contact area of the fabric, that is, the area formed by the knuckle surfaces of the fabric that the web contacts in the papermaking process. Further, the softness, absorbency, and caliper of the paper products may be influenced by the size of the pockets in the fabric. The planar volumetric index provides an indication of the contact area and pocket size, as the planar volumetric index is calculated as the contact area ratio (CAR) (as set forth in TABLE 1 above) multiplied by the effective pocket volume (EPV) multiplied by one hundred, i.e., CAR×EPV×100. The contact, area ratio and the effective pocket volume may be calculated using the techniques described above, and thereafter the planar volumetric index for the fabric may easily be calculated.

As will certainly be appreciated by those skilled in the art, knowing characteristics of the knuckles and pockets of a fabric, such as knuckle and pocket sizes and densities, provides a deep understanding of the fabric. One example of the application using the characteristics involves developing correlations between certain contact surface characteristics and resulting paper products. With the correlations, further fabric configurations can be developed, and those configurations can be characterized without testing a full-scale fabric on a papermaking machine. Thus, the techniques described above for determining contact surface characteristics of a fabric may save time and resources for both fabric manufacturers and/or paper producers that are experimenting with different fabrics.

The above-above described techniques can also be used in methods of analyzing the wear on a papermaking fabric. In one such method, a first representation of the knuckles in a portion of the fabric is formed in a medium. This first representation may be a print on a pressure measurement film, or the representation may be a photograph of a portion of the fabric and stored in a camera. A first image is generated of the knuckles of the fabric based on the first representation, such as by scanning the pressure measurement film or downloading the photograph from the camera. From the generated image, at (east one characteristic related to the contact area of the fabric may be determined as described above. The fabric may then be subjected to wearing. If the fabric is mounted on a papermaking machine, the wearing may come about simply by operating the papermaking machine. Alternatively, a simulated wearing may be performed on the fabric by sanding or grinding.

After the fabric is worn, the process of obtaining an image of a portion of the fabric and determining contact surface characteristics is again performed. That is, a second representation of the knuckles in the portion of the fabric is formed in a medium, which is used to generate a second image, which in turn is analyzed to determine the surface characteristics of the film. In this regard, the second representation may or may not be taken from the same portion of the fabric as the first representation. It would be expected that knuckles in the fabric would increase in size as a result of the wearing. Further, new knuckles may be formed in the fabric. As part of the contact surface characterization, increases in the knuckle sizes can be quantified by comparing the analysis of the second image after wearing and the first image before wearing. Such a process of wearing the fabric and thereafter determining the contact surface characteristics may be repeated any number of times, and with any given amount of wearing between each analysis.

A further part of analyzing the wear on tire fabric includes correlating the paper products made using the fabric with the changes in the contact surface due to the wearing. For example, before the first representation is taken of the fabric, a paper product is formed using the fabric. Properties of the paper product, such as the size of domes in the product or the caliper of the product, are then correlated with the contact surface characteristics determined through analysis of the first image formed by the first representation. A second paper product is then formed using the fabric, after the fabric is subject to wearing and before the second representation is taken of the fabric. Properties of the second-formed paper product are then correlated with the contact surface characteristics determined through analysis of the second image. Thus, an understanding can be achieved of how the formed paper product changes as the particular fabric configuration is worn.

In further aspects of the invention, the above-described techniques and processes may be used to compare different portions of a fabric, particularly, after the fabric runs on a papermaking machine over periods of time, it is known that different portions of a fabric will often show different wearing due to inconsistencies in the track that the fabric follows in the papermaking machine. According to different embodiments, the surface characterization techniques can be applied, for example, to different portions of a fabric before and after the fabric is run on a papermaking machine. Alternatively, the surface characterization techniques can be applied to different portions of the fabric while the fabric is still mounted on the papermaking machine. Thus, an understanding can be achieved of how different portions of a fabric are worn in a papermaking machine.

Figure 10A:
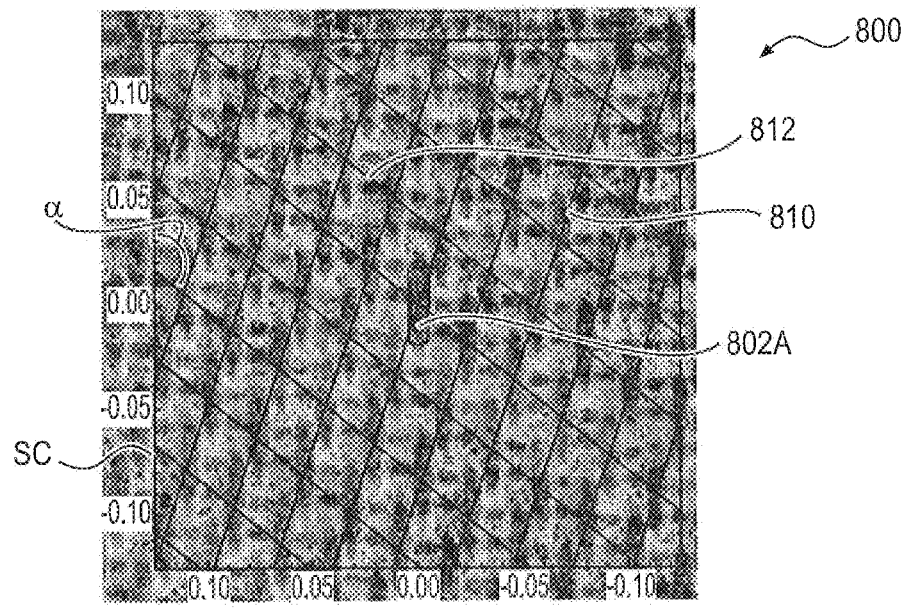
FIGS. 10A and 10B show the application of the analytic techniques applied to an image of a paper product.
Figure 10B:
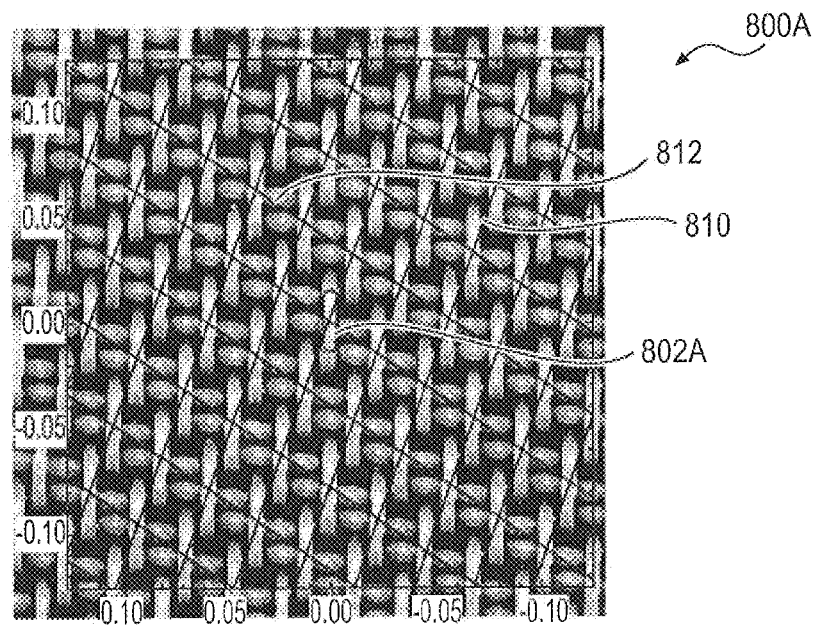

According to yet another aspect of the invention, the contact surface characterization can be used to obtain a fabric for making a paper product with a particular three-dimensional structure. FIGS. 10A and 10B demonstrate such a process. FIG. 10A shows an example of an image 800 of a paper product that is analyzed using the above-described techniques. Notably, the paper product has a three-dimensional structure that includes a plurality of domes separated by land areas. As described above, such a paper product can be made using a structuring fabric. If, however, the specific structuring fabric configuration that was used to make such a product was not known, a process according to the invention can be used to identify the structuring fabric configuration. As shown in FIG. 10A, an outline 802A can be drawn on the image of the paper product using the analysis program in a land area of the paper product, which corresponds to the position of a knuckle in the structuring fabric used to make the paper product. Further, a coordinate system including guidelines 812 and 814 can be drawn through the outline 802A, and the positions that correspond to other knuckles. Note that the domes in the paper product correspond to the pockets in the structuring fabric, and accordingly, the coordinate system is drawn without passing through the domes.

After the outline 802A is formed and the coordinate system with guidelines 812 and 814 are drawn, as shown in FIG. 10A, the outline 802A and coordinate system may be matched to images of fabrics so as to determine a configuration that produces the three-dimensional structure of the paper product. An example of such a match is shown in FIG. 10B, wherein the outline 802A of and coordinate system with guidelines 812 and 814 are overlaid upon an image 800A of a fabric. Note that the outline 802A matches the size and shape of a knuckle in the fabric, and that the guidelines pass through the knuckles, but not the areas that correspond to pockets in the fabric. This matching indicates that the fabric shown in image 800A could be used to produce a paper product similar to that shown in image 800.

Matching the outline and coordinate system from a paper product to a particular fabric may be facilitated by creating a searchable database of known fabrics. Such a database would include the previously-determined contact surface characteristics of fabrics, such the knuckle sizes, locations, pocket sizes, etc. After determining the sizes and positions for the knuckles and pockets of the fabric from the outline and coordinate system formed from the paper product, the database could be searched for fabrics with similar sizes and positions of knuckles and pockets.

To facilitate the process of matching an analyzed image of a paper product with a fabric, additional parameters may be used that are developed in the analysis of the paper product. One such additional parameter is the frequency that one set of guidelines crosses a guideline from the other set of guidelines. Note, a "set" of guidelines refers to parallel guidelines, e.g., the guideline 812 and all the guidelines parallel thereto to form a set. In FIG. 8A, die frequency of the set of guidelines that includes guideline 812 would be calculated, for example, having the analysis program determining the distance between two of the guidelines crossing guideline 810, as measured along one guideline 810. For example, if the guidelines crossing guideline 810 were spaced 0.130 cm apart as measured along the guideline 810, then the crossing guidelines would have a frequency of 7.7 cm$^{-1}$ (1/0.130 cm). A similar frequency calculation could be done for the other set of guidelines that cross guideline 812 by measuring the spacing between the guidelines of this set along one of the guideline 812. Once determined, the frequency in the guideline spacing for a paper product could be matched to the previously determined frequency of guideline spacing for fabrics, which have been stored in a searchable database.

Another parameter that can be calculated to facilitate the process of matching the outlined knuckle and guidelines from a paper product to a particular fabric is the angle to the guidelines of a set from a reference line. For example, the scale line SC in FIG. 10A could be used as a reference, and the angle α could be determined between the scale line SC and one set of the guidelines. The angle from die scale line SC to the other set of guidelines could also be determined. Once determined, the angles from the reference to the sets of guidelines for a paper product could be matched to the previously determined angles from the reference to the sets of guidelines for fabrics, which have been stored in a searchable database.

While the above-described methods are described in terms of matching a paper product to a known fabric, it will be readily appreciated that other embodiments include selecting a known fabric made on a desired, but not yet produced, three-dimensional paper structure. That is, an outline knuckle or knuckles could be created in a blank image, and a knuckle and pocket pattern could be created by drawing guidelines in the blank image. The created image could then be matched with a known fabric in the manner described above.

In yet another embodiment, a fabric could be designed and manufactured based on the analysis of a paper product image or based on a created image representing a knuckle and pocket configuration. In this method, warp and weft yarns are chosen to correspond to the desired knuckle and pocket configuration, as determined by analysis of the paper product image or created in a blank image. Techniques for producing fabrics with particular weave patterns of warp and weft yarns are well known in the art. Thus, a fabric could be produced with the chosen warp and weft yarn configuration.

In other embodiments of my invention, the fabric characterization techniques described herein can be used to modify the configuration of a first papermaking fabric in order to produce a new, second papermaking fabric having different characteristics. In these embodiments, at least one knuckle or pocket characteristic of the first papermaking fabric is determined with the above-described techniques. The characteristic may be, for example, one or more of the characteristics described in TABLE 1 above. Further, die characteristic may be the pocket depth or effective pocket volume, which are determined according to the above-described techniques. Based on the determined characteristic(s), a modified fabric design is created wherein the characteristic(s) are changed. For example, the pocket depth may be increased from the pocket depth measured in the first papermaking fabric. Those skilled in the art will appreciate the factors that determine the characteristics of a papermaking fabric, and as such, will appreciate how the design of the first papermaking fabric may be altered to produce the new papermaking fabric having the different characteristics. For example, an aspect of the fabric such as one or more of yarn diameters, yarn densities, yarn shapes, weave patterns, and the heat setting used to bond the yarns together, could be altered to produce the second papermaking fabric that has the modified characteristics(s). One of many examples of papermaking fabric manufacturing techniques utilizing some of these factors can be seen in U.S. Pat. No. 6,350,336, the disclosure of which is incorporated by reference in its entirety.

In addition to, or in conjunction with, the embodiments for modifying the configuration a papermaking fabric design, the characteristics of paper products made using the structuring fabrics can be used in the development of a papermaking fabric having particular characteristics. For example, the characteristics of a first papermaking fabric can be determined using the above-described techniques. The first papermaking fabric can also be used to make a papermaking product, for example, using the papermaking methods described above. The characteristics of the paper product can then be determined, and thereafter correlated with the determined characteristics of the first papermaking fabric. For example, the densities and heights of the domes formed in the paper product can be measured by examining the domes with a microscope. As discussed above, the domes are formed in the pockets of the papermaking fabric. It follows that the pocket density and pocket depth determined in a papermaking fabric can be correlated to a dome density and dome height found in a paper product that was made using the papermaking fabric. Such correlations can then be used to determine what paper product could be expected to be made with another papermaking fabric having comparable characteristics. Further, as described above, a new papermaking fabric design could be developed, with adjusted characteristics in order to produce paper products with modified characteristics as desired.

Although this invention has been described in certain specific exemplary embodiments, many additional modifications and variations would be apparent to those skilled in the art in light of this disclosure. It is, therefore, to be understood that this invention may be practiced otherwise than as specifically described. Thus, the exemplary embodiments of the invention should be considered in all respects to be illustrative and not restrictive, and the scope of the invention to be determined by any claims supportable by this application and the equivalents thereof, rather than by the foregoing description.

I claim:

1. A process of determining features of a fabric, the process comprising:
    forming a representation of a portion of a surface of the fabric, the representation (i) showing locations and sizes of knuckles and pockets in the surface of the fabric, and (ii) being formed by pressing the fabric against a pressure measurement film;
    generating an image of the portion of the fabric based on the representation;
    displaying at least a portion of the image on a screen associated with a computer having a processor;
    drawing an outline around at least one of the knuckles in the displayed image; and
    drawing guidelines in the displayed image such that the guidelines (i) pass through the center of the outlined knuckle, (ii) pass through the other knuckles, and (iii) do not pass through areas of the image that correspond to where the pockets are formed between the knuckles,
    wherein the outline and the guidelines are drawn using an image analysis program stored in a non-transitory computer-readable medium.

2. The process according to claim 1, further comprising a step of determining at least one of a length of the outlined knuckle, a width of the outlined knuckle, and locations of the knuckles along the guidelines, wherein the determining is made using the image analysis program.

3. The process according to claim 2, further comprising a step of calculating at least one of a percentage of the surface of the fabric that corresponds to the knuckles and the percentage of the surface of the fabric that corresponds to pockets, wherein the calculating uses the determinations of the length of the outlined knuckle, the width of the outlined knuckle, and the locations of the knuckles along the guidelines made by the image analysis program.

4. A process of determining features of a fabric, the process comprising:
    forming a representation of a portion of a surface of the fabric, the representation showing locations and sizes of knuckles and pockets in the surface of the fabric;
    generating an image of the portion of the fabric based on the representation, the image being made at a specific scale relative to the representation;
    displaying at least a portion of the image on a screen associated with a computer having a processor;
    drawing an outline around at least one of the knuckles in the displayed image;
    drawing guidelines in the displayed image such that the guidelines (i) pass through the center of the outlined knuckle, (ii) pass through the other knuckles, and (iii) do not pass through areas of the image that correspond to where the pockets are formed between the knuckles; and
    calculating a property of the fabric using the outlined knuckle, the guidelines, and the scale of the image relative to the representation,
    wherein the outline and the guidelines are drawn using an image analysis program stored in a non-transitory computer-readable medium.

5. The process according to claim 4, wherein the scale of the image relative to the representation is input into the image analysis program.

6. The process according to claim 4, wherein the display of the image is provided at a first magnification when the outline around the knuckle is drawn, the display of the image is provided at a second magnification when the guidelines are drawn, and the first magnification is greater than the second magnification.

7. The process according to claim 4, wherein the drawing step comprises drawing outlines around a plurality of knuckles.

8. The process according to claim 4, wherein the image analysis program determines positions of knuckles using the guidelines.

9. The process according to claim 4, wherein the step of calculating a property of the fabric includes:
    (i) a step of determining at least one of a length of the outlined knuckle, a width of the outlined knuckle, and locations of the knuckles along the guidelines, wherein the determination is made by the image analysis program; and
    (ii) a step of calculating at least one of a percentage of the surface of the fabric that corresponds to the knuckles and the percentage of the surface of the fabric that corresponds to pockets.

10. A process of determining features of a fabric, the process comprising:
    forming a representation of a portion of a surface of the fabric, the representation showing locations and sizes of knuckles and pockets in the surface of the fabric;
    generating an image of the portion of the fabric based on the representation;
    displaying at least a portion of the image on a screen associated with a computer having a processor;
    drawing an outline around at least one of the knuckles in the displayed image; and
    drawing a coordinate system of guidelines in the displayed image such that the guidelines (i) pass through the center of the outlined knuckle, (ii) pass through the centers of other knuckles, and (iii) do not pass through areas of the image that correspond to where the pockets are formed between the knuckles, wherein the guidelines cross each other at points corresponding to knuckles,
    wherein the outline and the guidelines are drawn using an image analysis program stored in a non-transitory computer-readable medium, and
    wherein the image analysis program determines the sizes of knuckles based on the outlined knuckle and determines the positions of knuckles based on the coordinate system of guidelines.

11. The process according to claim 10, further comprising calculating a property of the fabric using the outlined knuckle, the guidelines, and a frequency of the guidelines.

12. The process according to claim 11, wherein the step of calculating a property of the fabric includes:
    (i) a step of determining at least one of a length of the outlined knuckle, a width of the outlined knuckle, and locations of the knuckles along the guidelines, wherein the determination is made by the image analysis program; and
    (ii) a step of calculating at least one of a percentage of the surface of the fabric that corresponds to the knuckles and the percentage of the surface of the fabric that corresponds to the pockets.

13. The process according to claim 10, wherein the display of the image is provided at a first magnification when the outline around the knuckle is drawn, the display of the image is provided at a second magnification when the guidelines are drawn, and the first magnification is greater than the second magnification.

14. The process according to claim 10, wherein the drawing step comprises drawing outlines around a plurality of knuckles.

15. A process of determining features of a fabric, the process comprising:
    forming a representation of a portion of a surface of the fabric, the representation showing locations and sizes of knuckles and pockets in the surface of the fabric;
    generating an image of the portion of the fabric based on the representation;
    displaying at least a portion of the image on a screen associated with a computer having a processor;
    drawing an outline around at least one of the knuckles in the displayed image by (i) forming an initial outline around the knuckle, and (ii) reshaping the initial outline of the knuckle to more closely correspond to the shape of the knuckle, wherein the image is displayed at a first magnification on the screen when the outline is drawn; and
    drawing guidelines in the displayed image such that the guidelines (i) pass through the center of the outlined knuckle, (ii) pass through the other knuckles, and (iii) do not pass through areas of the image that correspond to where the pockets are formed between the knuckles, wherein the image is displayed at a second magnification on the screen when the guidelines are drawn, with the second magnification being less than the first magnification,
    wherein the outline and the guidelines are drawn using an image analysis program stored in a non-transitory computer-readable medium.

16. The process according to claim 15, wherein the initial outline is a shape stored in the image analysis program.

17. The process according to claim 15, wherein the drawing step comprises drawing outlines around a plurality of knuckles.

18. The process according to claim 15, wherein the image analysis program identifies the positions of knuckles using the guidelines.

19. The process according to claim 15, further comprising a step of determining at least one of a length of the outlined knuckle, a width of the outlined knuckle, and locations of the knuckles along the guidelines, wherein the determining is made using the image analysis program.

20. The process according to claim 19, further comprising a step of calculating at least one of a percentage of the surface of the fabric that corresponds to the knuckles and the percentage of the surface of the fabric that corresponds to pockets, wherein the calculating uses the determinations of the length of the outlined knuckle, the width of the outlined knuckle, and the locations of the knuckles along the guidelines made by the image analysis program.

21. A process of determining features of a fabric, the process comprising:
- forming a representation of a portion of a surface of the fabric, the representation (i) showing locations and sizes of knuckles and pockets in the surface of the fabric, and (ii) being formed by pressing the fabric against wax paper;
- generating an image of the portion of the fabric based on the representation;
- displaying at least a portion of the image on a screen associated with a computer having a processor;
- drawing an outline around at least one of the knuckles in the displayed image; and
- drawing guidelines in the displayed image such that the guidelines (i) pass through the center of the outlined knuckle, (ii) pass through the other knuckles, and (iii) do not pass through areas of the image that correspond to where the pockets are formed between the knuckles,
- wherein the outline and the guidelines are drawn using an image analysis program stored in a non-transitory computer-readable medium.

22. The process according to claim 21, further comprising a step of determining at least one of a length of the outlined knuckle, a width of the outlined knuckle, and locations of the knuckles along the guidelines, wherein the determining is made using the image analysis program.

23. The process according to claim 22, further comprising a step of calculating at least one of a percentage of the surface of the fabric that corresponds to the knuckles and the percentage of the surface of the fabric that corresponds to pockets, wherein the calculating uses the determinations of the length of the outlined knuckle, the width of the outlined knuckle, and the locations of the knuckles along the guidelines made by the image analysis program.

\* \* \* \* \*